US012685774B2

(12) United States Patent
Xiao et al.

(10) Patent No.: US 12,685,774 B2
(45) Date of Patent: Jul. 21, 2026

(54) CELL/GENE THERAPIES TARGETING MAGE-A4 PEPTIDE

(71) Applicants:Innovative Cellular Therapeutics Holdings, Ltd., George Town (KY); Innovative Cellular Therapeutics, Inc., Rockville, MD (US)

(72) Inventors: Lei Xiao, Rockville, MD (US); Chengfei Pu, Shanghai (CN); Zhiyuan Cao, Shanghai (CN); Xiaogang Shen, Shanghai (CN); Dongqi Chen, Shanghai (CN); Beibei Jia, Shanghai (CN); Le Tian, Rockville, MD (US)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 664 days.

(21) Appl. No.: 18/008,911

(22) PCT Filed: Jun. 9, 2021

(86) PCT No.: PCT/US2021/036650
§ 371 (c)(1),
(2) Date: Dec. 7, 2022

(87) PCT Pub. No.: WO2021/252654
PCT Pub. Date: Dec. 16, 2021

(65) Prior Publication Data
US 2023/0293691 A1      Sep. 21, 2023

Related U.S. Application Data

(60) Provisional application No. 63/134,313, filed on Jan. 6, 2021, provisional application No. 63/037,758, filed on Jun. 11, 2020.

(51) Int. Cl.
| | |
|---|---|
| *A61K 40/11* | (2025.01) |
| *A61K 40/31* | (2025.01) |
| *A61K 40/42* | (2025.01) |
| *A61P 35/00* | (2006.01) |
| *A61P 37/04* | (2006.01) |
| *C07K 14/47* | (2006.01) |
| *C07K 14/705* | (2006.01) |
| *C07K 16/30* | (2006.01) |
| *C12N 5/0783* | (2010.01) |
| *A61K 38/00* | (2006.01) |
| *A61K 39/00* | (2006.01) |

(52) U.S. Cl.
CPC .......... *A61K 40/4268* (2025.01); *A61K 40/11* (2025.01); *A61K 40/31* (2025.01); *A61P 35/00* (2018.01); *A61P 37/04* (2018.01); *C07K 14/4748* (2013.01); *C07K 14/7051* (2013.01); *C07K 14/70521* (2013.01); *C07K 14/70578* (2013.01); *C07K 16/30* (2013.01); *C12N*
*5/0636* (2013.01); *A61K 38/00* (2013.01); *A61K 2039/505* (2013.01); *A61K 2239/13* (2023.05); *A61K 2239/21* (2023.05); *A61K 2239/22* (2023.05); *A61K 2239/31* (2023.05); *A61K 2239/38* (2023.05); *C07K 2317/622* (2013.01); *C07K 2317/76* (2013.01); *C07K 2319/02* (2013.01); *C07K 2319/03* (2013.01); *C07K 2319/33* (2013.01)

(58) Field of Classification Search
CPC .... A61K 40/4268; A61K 40/11; A61K 40/31; C07K 14/4748; C07K 14/7051; C07K 14/70521; C07K 14/70578
See application file for complete search history.

(56) References Cited

U.S. PATENT DOCUMENTS

| | | | |
|---|---|---|---|
| 2004/0033541 A1 | 2/2004 | Zhang et al. | |
| 2018/0179283 A1 | 6/2018 | Peled Kamar et al. | |
| 2018/0282418 A1 | 10/2018 | Bicknell et al. | |
| 2019/0030151 A1* | 1/2019 | Jones .................... | A61K 40/11 |
| 2019/0048085 A1 | 2/2019 | Dotti et al. | |

FOREIGN PATENT DOCUMENTS

WO      WO 2018102795 A2      6/2018

OTHER PUBLICATIONS

Duffour et al. A MAGE-A4 peptide presented by HLA-A2 is recognized by cytolytic T lymphocytes. Eur. J. Immunol. 1999. 29: 3329-3337 (Year: 1999).*

Sanderson et al. Preclinical evaluation of an affinity-enhanced MAGE-A4-specific T-cell receptor for adoptive T-cell therapy. Oncoimmunology 2020, vol. 9, No. 1, e1682381, p. 1-11 (Year: 2020).*

Kageyama, et al., "Adoptive Transfer of MAGE-A4 T-cell Receptor Gene-Transduced Lymphocytes in Patients with Recurrent Esophageal Cancer." May 2015. Clin Cancer Res. 21(10):2268-2277.

Ounap, et al., "Antibody Response Against Cancer-testis Antigens MAGEA4 and MAGEA10 in Patients with Melanoma." Jul. 2018. Oncology Letters. 16(1):211-218.

Sun, et al., "T-cell Receptor Gene Therapy Targeting Melanoma-associated Antigen-A4 by Silencing of Endogenous TCR Inhibits Tumor Growth in Mice and Human." Jun. 2019. Cell Death & Disease. 10(7):1-10.

International Search Report and Written Opinion mailed Oct. 27, 2021 in International Application No. PCT/US2021/036650, 12 pages.

* cited by examiner

*Primary Examiner* — Taeyoon Kim
(74) *Attorney, Agent, or Firm* — Lee & Hayes, P.C.

(57) ABSTRACT

The present disclosure relates to compositions and methods for treating a subject having cancer associated with melanoma-associated antigen 4 (MAGE-A4) peptide. The disclosure includes the embodiments relate to a chimeric antigen receptor (CAR) that binds MAGE-A4 peptide, a polynucleotide encoding a CAR that binds the MAGE-A4 peptide, a modified cell comprising a CAR that binds the MAGE-A4 peptide, and a population of modified cells comprising a CAR that binds the MAGE-A4 peptide.

20 Claims, 9 Drawing Sheets

Specification includes a Sequence Listing.

CELL/GENE THERAPIES TARGETING MAGE-A4 PEPTIDE

CROSS REFERENCE TO RELATED APPLICATIONS

This application is a U.S. National Phase Application of International Application No. PCT/US2021/036650 filed Jun. 9, 2021, which claims the benefit of U.S. Provisional Application No. 63/037,758, filed Jun. 11, 2020; and U.S. Provisional Application No. 63/134,313, filed Jan. 6, 2021; all of which are incorporated herein by reference in their entirety.

SEQUENCE LISTING INFORMATION

A computer readable textfile, entitled "sDS1.0099PCT_ST25.txt," created on or about May 24, 2021, with a file size of about 35.7 KB, contains the sequence listing for this application and is hereby incorporated by reference in its entirety.

TECHNICAL FIELD

The present disclosure relates to compositions and methods for expanding and maintaining modified cells, including genetically modified cells and uses thereof, to treat diseases, including cancer.

BACKGROUND

Cancer is characterized by the abnormal growth of cells that invade or spread to other parts of the body. In humans, there are more than one hundred types of cancer. One example is lung cancer occurring in the tissue of the lungs. Since lung cancer cells lose the characteristics of normal cells, the connection between lung cancer cells is lost. Once cancer cells are exfoliated, they spread over the entire body via the blood and/or lymph systems and become life-threatening. Currently, lung cancer is the leading cause of cancer death among men and women and is the second most common cancer in both men and women. Melanoma antigen family A4 (MAGE-A4) has been reported to be overexpressed in a number of malignant cancers including lung cancer, colon cancer, and bladder cancer. Thus, MAGE-A4 is an immunotherapy target for various malignant tumors, including non-small cell lung cancer.

SUMMARY

The present disclosure describes a chimeric antigen receptor (CAR), wherein the CAR comprises an extracellular domain, a transmembrane domain, and an intracellular domain, and wherein the extracellular domain comprises amino acid sequence SEQ ID NO: 10 or 13. In embodiments, the CAR binds MAGE-A4. In embodiments, the CAR binds to the MAGE-A4 peptide comprising amino acid sequence SEQ ID NO: 14. In embodiments, the CAR comprises amino acid sequence SEQ ID NO: 11 or 12. In embodiments, the CAR comprises amino acid sequence SEQ ID NO: 15, 16, or 17.

Embodiments describe a composition comprising the CAR described herein and a carrier. Embodiments describe a pharmaceutical composition comprising the CAR described herein and a pharmaceutically acceptable carrier. Embodiments describe a nucleic acid encoding the CAR above. Embodiments describe a vector, a cell, or a population of cells comprising the nucleic acid encoding the CAR above. In embodiments, the population of cells comprises T cells. Embodiments describe a pharmaceutical composition comprising the population of T cells above. Embodiments describe a method of stimulating an anti-tumor immune response in a subject in need thereof, the method comprising administering an effective amount of the pharmaceutical composition described herein to the subject, thereby stimulating an anti-tumor immune response. In embodiments, the subject is diagnosed with lung cancer, colon cancer, or bladder cancer. Embodiments describe a method of stimulating an immune response in a population of cells expressing MAGE-A4 peptide, the method comprising contacting the population of cells expressing MAGE-A4 peptide with an effective amount of the pharmaceutical composition above.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
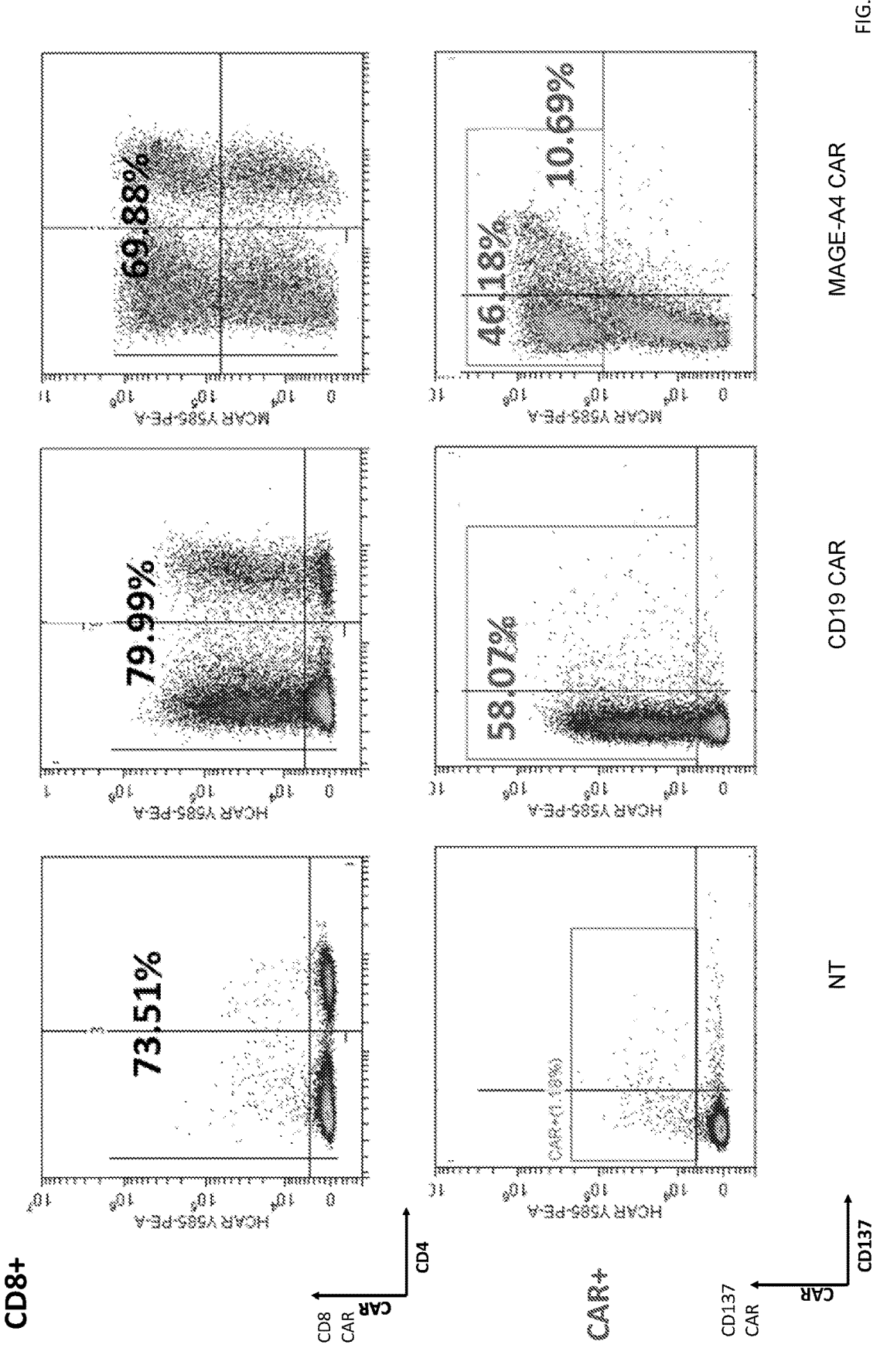
FIG. 1 shows flow cytometry results of the expression of CAR and CD137 on T cells.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the present disclosure, the following terms are defined below.

The articles "a" and "an" are used herein to refer to one or more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and $F(ab')_2$ fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', $F(ab')_2$, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in a tight, non-covalent association. The folding of these two domains emanates six hypervariable loops (3 loops each from the H and L chain) that contribute amino acid residues for antigen binding and confer antigen binding specificity antibody. However, even a single variable domain (or half of an Fv including only three complementarity determining regions (CDRs) specific for an antigen) can recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

The term "synthetic antibody" refers to an antibody that is generated using recombinant DNA technology, such as, for example, an antibody expressed by a bacteriophage. The term also includes an antibody generated by the synthesis of a DNA molecule encoding the antibody and the expression of the DNA molecule to obtain the antibody or obtain an amino acid encoding the antibody. The synthetic DNA is obtained using technology that is available and well known in the art.

The term "antigen" refers to a molecule that provokes an immune response, which may involve either antibody production, or the activation of specific immunologically competent cells, or both. Antigens include any macromolecule, including all proteins or peptides or molecules derived from recombinant or genomic DNA. For example, DNA including a nucleotide sequence or a partial nucleotide sequence encoding a protein or peptide that elicits an immune response, and therefore, encodes an "antigen," as the term is used herein. An antigen need not be encoded solely by a full-length nucleotide sequence of a gene. An antigen can be generated, synthesized, or derived from a biological sample including a tissue sample, a tumor sample, a cell, or a biological fluid.

The term "anti-tumor effect," as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies to prevent the occurrence of tumor in the first place.

The term "auto-antigen" refers to an endogenous antigen mistakenly recognized by the immune system as foreign. Auto-antigens include cellular proteins, phosphoproteins, cellular surface proteins, cellular lipids, nucleic acids, glycoproteins, including cell surface receptors.

The term "autologous" describes a material derived from a subject subsequently re-introduced into the same subject.

The term "allogeneic" describes a graft derived from a different subject of the same species. For example, a donor subject may be related or unrelated to the recipient subject, but the donor subject has immune system markers similar to the recipient subject.

The term "xenogeneic" describes a graft derived from a subject of a different species. For example, the donor subject is from a different species than a recipient subject, and the donor subject and the recipient subject can be genetically and immunologically incompatible.

The term "cancer" refers to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes," and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that those other elements are optional and may or may not be present depending upon whether they affect the listed elements' activity or action.

The terms "complementary" and "complementarity" refer to polynucleotides (i.e., a sequence of nucleotides) related to the base-pairing rules. For example, the sequence "A-G-T" is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands significantly affects the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "co-stimulatory ligand" refers to a molecule on an antigen-presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which, combined with a primary signal, such as TCR/CD3 ligation, leads to T cell proliferation and/or upregulation or down-regulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated, then the subject's health continues to deteriorate. In contrast, a "disorder" in a subject is a state of health in which the animal can maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. About polynucleotides and proteins, the term "endogenous" or "native" refers to naturally occurring polynucleotide or amino acid sequences that may be found in a given wild-type cell or organism. Also, a particular polynucleotide sequence isolated from a first organism and transferred to a second organism by molecular biological techniques is typically considered an "exogenous" polynucleotide or amino acid sequence for the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, the term "expression" refers to expression or overexpression.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

Viruses can deliver nucleic acids into a cell in vitro and in vivo (in a subject). Examples of viruses useful for delivering nucleic acids into cells include retrovirus, adenovirus, herpes simplex virus, vaccinia virus, and adeno-associated virus.

There are also non-viral methods for delivering nucleic acids into a cell, such as electroporation, gene gun, sonoporation, magnetofection, and oligonucleotides, and lipoplexes, dendrimers, and inorganic nanoparticles.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig" refers to a class of proteins, which function as antibodies. The five members included in this class of proteins are IgA, IgG, IgM, IgD, and IgE. IgA is the primary antibody present in body secretions, such as saliva, tears, breast milk, gastrointestinal secretions, and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a substantially or essentially free material from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment that has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment and association with other components of the cell.

The term "substantially purified" refers to a substantially free material from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that degenerate versions of each other and encode the same amino acid sequence. The phrase nucleotide sequence that encodes a protein or an RNA may also include introns to the extent that the nucleotide sequence encoding the protein may, in some version, contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, lentiviruses enable the integration of the genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating" refers to mediating a detectable increase or decrease in the level of a response in a subject compared with the level of a response in the subject in the absence of a treatment or compound and/or compared with the level of a response in an otherwise identical but untreated subject. The term encompasses perturbing and/or affecting a native signal or response, thereby mediating a beneficial therapeutic response in a subject, preferably a human.

Nucleic acid is "operably linked" when placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence, or a ribosome binding site is operably linked to a coding sequence if it is positioned to facilitate translation.

The term "under transcriptional control" refers to a promoter being operably linked to and in the correct location and orientation about a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having a solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms tumor, cervical cancer, testiculartumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal Cancer |
| MUC12 | colorectal Cancer |
| GUCY2C | colorectal Cancer |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer, and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesotelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinoma |
| EpCAM | Carcinoma |
| EGFRvIII | Glioma-Glioblastoma |
| EGFR | Glioma-NSCL cancer |
| tMUC1 | Cholangiocarcinoma, Pancreatic cancer, Breast |
| PSCA | pancreas, stomach, or prostate cancer |
| FCER2, GPR18, FCRLA, CXCR5, FCRL3, FCRL2, HTR3A, and CLEC17A | breast cancer |
| TRPMI, SLC45A2, and SLC24A5 | Lymphoma |
| DPEP3 | Melanoma |
| KCNK16 | ovarian, testis |
| LIM2 or KCNV2 | pancreatic |
| SLC26A4 | thyroid cancer |
| CD171 | Neuroblastoma |
| Glypican-3 | Sarcoma |
| IL-13 | Glioma |

TABLE 1-continued

| Solid Tumor antigen | Disease tumor |
|---|---|
| CD79a/b | Lymphoma |
| MAGE-A4 peptide | Lung cancer, colon cancer, bladder cancer, etc. |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human or animal, amenable to the methods described herein. In embodiments, the patient, subject, or individual is a human or animal. In embodiments, the term "subject" is intended to include living organisms in which an immune response can be elicited (e.g., mammals). Examples of subjects include humans, and animals, such as dogs, cats, mice, rats, and transgenic species.

A subject in need of treatment or need thereof includes a subject having a disease, condition, or disorder that needs to be treated. A subject in need thereof also includes a subject that needs treatment to prevent a disease, condition, or disorder.

The term "polynucleotide" or "nucleic acid" refers to mRNA, RNA, cRNA, rRNA, cDNA, or DNA. The term typically refers to a polymeric form of nucleotides of at least 10 bases in length, ribonucleotides or deoxynucleotides, or a modified form of either type of nucleotide. The term includes all forms of nucleic acids, including single and double-stranded forms of nucleic acids.

The terms "polynucleotide variant" and "variant," and the like refer to polynucleotides displaying substantial sequence identity with a reference polynucleotide sequence or polynucleotides that hybridize with a reference sequence under stringent conditions that are defined hereinafter. These terms also encompass polynucleotides distinguished from a reference polynucleotide by the addition, deletion, or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity about the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In embodiments, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions. In this regard, it is well understood in the art that some amino acids may be changed to others with broadly similar properties without changing the nature of the polypeptide activity. Polypeptide variants also encompass polypeptides in which one or more amino acids have been added or deleted, or replaced with different amino acid residues.

The term "promoter" refers to a DNA sequence recognized by the cell's synthetic machinery or introduced synthetic machinery required to initiate the specific transcription of a polynucleotide sequence. The term "expression control (regulatory) sequences" refers to DNA sequences necessary to express an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein for an antibody, refers to an antibody that recognizes a specific antigen but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding" can be used about the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A) in a reaction containing labeled "A" and the antibody will reduce the amount of labeled A bound to the antibody.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount. It may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation" refers to a primary response induced by binding of a stimulatory molecule (e.g., a TCR/CD3 complex) with its cognate ligand, thereby mediating a signal transduction event, such as signal transduction via the TCR/CD3 complex. Stimulation can mediate altered expression of certain molecules, such as downregulation of TGF-β and/or reorganization of cytoskeletal structures.

The term "stimulatory molecule" refers to a molecule on a T cell that specifically binds a cognate stimulatory ligand present on an antigen-presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen-presenting cell (e.g., an APC, a dendritic cell, a B-cell, and the like.) can specifically bind with a cognate binding partner (referred to herein as a "stimulatory molecule") on a cell, for example, a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to treatment and/or prophylaxis. A therapeutic effect is obtained by suppressing, remission, or eradicating a disease state or alleviating the symptoms of a disease state.

The term "therapeutically effective amount" refers to the amount of the subject compound that will elicit the biological or medical response of a tissue, system, or subject sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease, its severity, and the age, weight, etc., of the subject to be treated.

The term "treat a disease" refers to reducing the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell has been transfected, transformed, or transduced with an exogenous nucleic acid. The cell includes the primary subject cell and its progeny.

The term "vector" refers to a polynucleotide that comprises an isolated nucleic acid and can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted, making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges and individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain, and a cytoplasmic domain or intracellular domain. In embodiments, the domains of the CAR are on the same polypeptide chain, for example, a chimeric fusion protein. In embodiments, the domains are on different polypeptide chains, for example, the domains are not contiguous.

The extracellular domain of a CAR molecule includes an antigen binding domain. The antigen binding domain is for expanding and/or maintaining the modified cells, such as a CAR T cell, or killing a tumor cell, such as a solid tumor. In embodiments, the antigen binding domain for expanding and/or maintaining modified cells binds an antigen, for example, a cell surface molecule or marker, on the surface of a WBC.

The cells described herein, including modified cells such as CAR cells and modified T cells, can be derived from stem cells. Stem cells may be adult stem cells, embryonic stem cells, particularly non-human stem cells, cord blood stem cells, progenitor cells, bone marrow stem cells, and induced pluripotent totipotent stem cells, or hematopoietic stem cells. A modified cell may also be a dendritic cell, an NK cell, a B cell, or a T cell selected from the group consisting of inflammatory T lymphocytes, cytotoxic T lymphocytes, regulatory or helper T lymphocytes. In embodiments, Modified cells may be derived from the group consisting of CD4+ T lymphocytes and CD8+ T lymphocytes. Prior to the expansion and genetic modification of the cells of the invention, a source of cells may be obtained from a subject through a variety of non-limiting methods. T cells may be obtained from several non-limiting sources, including peripheral blood mononuclear cells, bone marrow, lymph node tissue, cord blood, thymus tissue, tissue from a site of infection, ascites, pleural effusion, spleen tissue, and tumors. In embodiments of the present invention, any number of T cell lines available and known to those skilled in the art may be used. In embodiments, modified cells may be derived from a healthy donor, from a patient diagnosed with cancer, or from a patient diagnosed with an infection. In embodiments, a modified cell is part of a mixed population of cells that present different phenotypic characteristics.

A population of cells refers to a group of two or more cells. The cells of the population could be the same, such that the population is a homogenous population of cells. The cells of the population could be different, such that the population is a mixed population or a heterogeneous population of cells. For example, a mixed population of cells could include modified cells comprising a first CAR and cells comprising a second CAR, wherein the first CAR and the second CAR bind different antigens.

The term "stem cell" refers to any of certain types of cell which have the capacity for self-renewal and the ability to differentiate into other kind(s) of a cell. For example, a stem cell gives rise either to two daughter stem cells (as occurs in vitro with embryonic stem cells in culture) or to one stem cell and a cell that undergoes differentiation (as occurs, e.g., in hematopoietic stem cells, which give rise to blood cells). Different categories of stem cells may be distinguished based on their origin and/or the extent of their capacity for differentiation into other types of cells. For example, stem cells may include embryonic stem (ES) cells (i.e., pluripotent stem cells), somatic stem cells, induced pluripotent stem cells, and any other types of stem cells.

The pluripotent embryonic stem cells are found in the inner cell mass of a blastocyst and have an innate capacity for differentiation. For example, pluripotent embryonic stem cells can form any type of cell in the body. When grown in vitro for long periods, ES cells maintain pluripotency as progeny cells retain the potential for multilineage differentiation.

Somatic stem cells can include fetal stem cells (from the fetus) and adult stem cells (found in various tissues, such as bone marrow). These cells have been regarded as having a lower capacity for differentiation than that of the pluripotent ES cells—with the capacity of fetal stem cells being greater than that of adult stem cells. Somatic stem cells apparently differentiate into only a limited number of types of cells and have been described as multipotent. The "tissue-specific" stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., PS cells or iPSCs) may include a type of pluripotent stem cell artificially derived from a non-pluripotent cell (e.g., an adult somatic cell) by inducing an expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be obtained from adult stomach, liver, skin, and blood cells.

In embodiments, the antigen binding domain for killing a tumor binds an antigen on the surface of a tumor, for example, a tumor antigen or tumor marker. Tumor antigens are proteins produced by tumor cells that elicit an immune response, particularly T cell mediated immune responses. Tumor antigens are well known in the art and include, for example, tumor associated MUC1 (tMUC1), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19 CAR or 19CAR, a CAR molecule that includes an antigen binding domain that binds CD19.

In embodiments, the antigen binding domain of the CAR described herein comprises antibodies, and non-antibody molecules. Examples of antibodies include a scFv (single-chain variable fragment), a heavy chain variable (VH) region, or a dual chain CAR. The antibodies can also include nanobodies such as a camelid heavy chain (VHH) antibody. Examples of non-antibody molecules include cytokines, natural ligand/receptors pairs (including innate immune receptors and TNF receptors and their ligands), growth factors, proteins, and peptides. Examples of cytokines include IL13, for example, IL13 E13Y mutein, for targeting IL13 receptor a2 on tumors. Examples of ligands/receptor pairs include NKG2D and its ligands. Examples of growth factors include VEGF, for targeting VEGF receptor on tumor cells. Examples of peptides include designed ankyrin repeat proteins (DARPins) and monobodies. Monobodies include synthetic binding proteins constructed using a fibronectin type III domain (FN3) as a molecular scaffold. For example, Adnectin™ is a monobody based on the 10t$^h$ fibronectin type III domain.

In embodiments, the extracellular antigen binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence (GGGGS)$_3$ (SEQ ID NO: 18), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides, preferably comprised of about 20 or fewer amino acid residues. The single chain variants can be produced either recombinantly or synthetically. For the synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect, or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains function to transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule.

In embodiments, the co-stimulatory molecules are cell surface molecules (other than antigens receptors or their ligands) required to activate a cellular response to an antigen.

In embodiments, the co-stimulatory domain includes the intracellular domain of CD27, CD28, 4-1BB (CD137), OX40, CD30, CD40, PD-1, ICOS, lymphocyte function-associated antigen-1 (LFA-1), CD2, CD7, CD40-MyD88, CD244, NKG2D, LIGHT, NKG2C, B7-H3, a ligand that specifically binds with CD83, or any combination thereof.

In embodiments, the signaling domain includes the signaling domain of CD3 zeta, DAP10, DAP12, FcεRIγ, Fyn, Lck, Syk, Zap70, or a combination thereof. In embodiments, the signaling domain includes CD3 zeta domain derived from a T cell receptor.

The CAR molecules described herein also include a transmembrane domain. The incorporation of a transmembrane domain in the CAR molecules stabilizes the molecule. In embodiments, the transmembrane domain of the CAR described herein comprises the transmembrane domain of CD28, 4-1BB, CD3ε, CD3ζ, CD4, CD7, CD8a, CD28, FcεRIγ, NKG2D, or OX40.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids. In embodiments, the spacer domain of the CAR described herein comprises a spacer domain of CD4, CD7, CD8, CD28, IgD, IgG1, or IgG4.

In embodiments, two different antigen binding domains can be on the same binding molecule, for example, on a bispecific CAR and encoded by a single nucleic acid. In embodiments, the bispecific CAR can have two different scFv molecules joined together by linkers. A bispecific CAR (or tandem CAR (tanCAR)) may include two binding domains: scFv1 and scFv2. In embodiments, scFv1 binds an antigen of a white blood cell (e.g., CD19), and scFv2 binds a solid tumor antigen (e.g., MAGE-A4 peptide). In embodiments, scFv1 binds a solid tumor antigen, and scFv2 binds another solid tumor antigen (e.g., MAGE-A4 peptide and CLDN 18.2). Claudin18.2 (CLDN 18.2) is a stomach-specific isoform of Claudin-18. CLDN 18.2 is highly expressed in gastric and pancreatic adenocarcinoma. In embodiments, scFv1 binds an antigen expressed on tumor cells but not on normal tissues (e.g., MAGE-A4 peptide); scFv2 binds an antigen expressed on nonessential tissues associated with solid tumor; and the killing of normal cells of the tissue does not cause a life-threatening event (e.g., complications) to the subject (e.g., TSHR, GUCY2C). Examples of the nonessential tissues include organs such as prostate, breast, or melanocyte. In embodiments, scFv1 and scFv2 bind to different antigens that are expressed on the same nonessential tissue (e.g., ACPP and SLC45A3 for Prostate cancer, and SIGLEC15 and UPK2 for Urothelial cancer).

In embodiments, the two different antigen binding domains can be on a CAR and/or a T cell receptor (TCR) and are encoded by separate nucleic acids. The binding domain of a TCR can target a specific tumor antigen or tumor marker on the cell of a tumor. In embodiments, the TCR binding domain is a TCR alpha binding domain or TCR beta binding domain that targets a specific tumor antigen. In embodiments, the TCR comprises the TCRγ and TCRδ chains or the TCRα and TCRμ chains.

The present disclosure describes compositions and methods of treating a subject having cancer associated with MAGE-A4 peptide, a protein normally expressed few normal tissue cells but present in certain cancers. Embodiments relate to a polynucleotide encoding a CAR binding MAGE-A4 peptide (MAGE-A4 CAR), a CAR binding MAGE-A4 peptide, a modified cell comprising a CAR binding MAGE-A4 peptide, and a population of modified cells comprising a CAR binding MAGE-A4 peptide.

HLA-peptide complex (HPC) refers to lymphocyte epitopes or antigens restricted by the HLA complex. For example, T cell epitopes are presented on the surface of an antigen-presenting cell, where they are bound to MHC molecules. In humans, professional antigen-presenting cells are specialized to present MHC class II peptides, whereas most nucleated somatic cells present MHC class I peptides. T cell epitopes presented by MHC class I molecules may typically include peptides between 8 and 11 amino acids in length, whereas MHC class II molecules present longer peptides, 13-17 amino acids in length, and non-classical MHC molecules also present non-peptidic epitopes such as glycolipids. In embodiments, an HPC may include α1, α2, and α3 domains, β-macroglobulin, and an antigen peptide. In embodiments, MAGE-A4 peptide comprise an HPC.

As a cancer/testis (CT) antigen, which is expressed only in human germ cells and various human cancers of the testis, MAGE-A4 (Melanoma antigen family A4), also known as melanoma-associated antigen 4, is recognized as a very safe cancer target. MAGE-A4 is expressed in various tumors, including 75% of esophageal carcinoma, 60% of head and neck cancer, 48% of non-small cell lung cancer, 33% of gastric cancer, and 21% of Hodgkin Disease, without any expression in normal tissues other than testis. Patients suffering from non-small cell lung carcinoma, head and neck cancer, and adult T-cell leukemia/lymphoma with the expression of MAGE-A4 usually develop spontaneously MAGE-A4-induced humoral or cellular immune responses. High expression of CT antigens such as MAGE-A4 in tumors may be associated with poor prognosis in patients with bladder cancer, ovarian cancer, non-small cell lung carcinoma, and head/neck cancer.

Some MAGE gene family proteins are only expressed in germ cells and cancer (MAGE-A to MAGE-C families). Others are widely expressed in normal tissues (MAGE-D through to MAGE-H). All these MAGE protein families have a homologous region that is closely matched to the sequence of the other MAGE proteins and comprises peptides displayed as HLA/peptide complexes in immune recognition. Hence, it is important to select TCR clinical candidates highly specific for the desired MAGE peptide/HLA-A2 antigen.

MAGE-A4 is a CTA member of the MAGE A gene family. The function is unknown, though it is thought that it may play a role in embryonal development. In tumor pathogenesis, it appears to be involved in tumor transformation or aspects of tumor progression. MAGE-A4 has been implicated in a large number of tumors, including seminoma, dyskeratosis congenital, melanoma, hepatocellular carcinoma, renal cell carcinoma, pancreatic cancer, lung cancer, colorectal cancer, and breast cancer.

MAGE-A4 comprises an HLA-restricted peptide antigen derived from MAGE-A4. More MAGE-A4 peptides and their antibodies can be found at WO2016/199141, incorporated herein by its reference. In embodiments, MAGE-A4 peptide refers to the peptide GVYDGREHTV (SEQ ID No: 14) corresponds to amino acid residue numbers 230-239 of the known MAGE-A4 protein.

The polynucleotide encoding the CAR binding MAGE-A4 peptide may further comprise a polynucleotide encoding one or more cytokines. The modified cell comprises the polynucleotide. The population of modified cells comprises the modified cell. In embodiments, the modified cells include one or more different antigen binding domains. The genetically modified cells can include at least two different antigen binding domains: a first antigen binding domain for expanding and/or maintaining the genetically modified cells and a second antigen binding domain for killing a target cell, such as a tumor cell. For example, the first antigen binding domain binds a surface marker, such as a cell surface molecule of a white blood cell (WBC), and the second antigen binding domain binds a target antigen of tumor cells. In embodiments, the cell surface molecule is a surface antigen of a WBC. A CAR can comprise the first or second antigen binding domain. The modified cells comprise the first and second antigen binding domains. In embodiments, the modified cells comprise modified cells comprising (1) a first group of modified cells comprising the first antigen binding domain and (2) a second group of modified cells comprising the second binding domain. In embodiments, the modified cells are a mixed population comprising two different groups of modified cells. The CAR can be a bispecific CAR. For example, the two antigen binding domains are on the same CAR (a bispecific CAR or tandem CAR (tanCAR)), on different CAR molecules, or on a CAR and T cell receptor (TCR). A single CAR can include at least two different antigen binding domains, or the two different antigen binding domains are each on a separate CAR.

Techniques of CARs binding MAGE-A4 peptide can be incorporated into CoupledCAR®. More information about CoupledCAR® can be found in PCT Publication NO: WO2020146743, which is incorporated by its entity.

Embodiments describe a method of stimulating a T cell-mediated immune response, the method comprising: contacting a population of cells comprising MAGE-A4 comprising the amino acid sequence of SEQ ID NO: 14 with a population of modified cells comprising a CAR binding the MAGE-A4 peptide, wherein the CAR comprises an extracellular domain, a transmembrane domain, and an intracellular domain, the extracellular domain comprising the amino acid sequences SEQ ID NO: 8 and SEQ ID NO: 9

Embodiments describe a method of treating a subject having a tumor expressing MAGE-A4 peptide, the method comprising: administering an effective amount of a pharmaceutical composition comprising a population of modified cells comprising a CAR binding the MAGE-A4 peptide, wherein the CAR comprises an extracellular domain, a transmembrane domain, and an intracellular domain, the extracellular domain comprising the amino acid sequences SEQ ID NO: 8 and SEQ ID NO: 9, and the MAGE-A4 peptide comprising the amino acid sequence of SEQ ID NO: 14. In embodiments, the CAR comprises at least one of the amino acid sequences SEQ ID NOs: 8-17.

In embodiments, the intracellular domain comprises one or more signaling domains, for example, one or more signaling domains of CD3 zeta, DAP10, DAP12, FcεRIγ, Fyn, Lck, Syk, and Zap70. In embodiments, the intracellular domain comprises a CD3 zeta signaling domain. In embodiments, the intracellular domain further comprises a co-stimulatory signaling region comprising an intracellular domain of a co-stimulatory molecule selected from the group consisting of CD27, CD28, 4-1BB (CD137), OX40, CD30, CD40, PD-1, ICOS, lymphocyte function-associated antigen-1 (LFA-1), CD2, CD7, CD40-MyD88, CD244, NKG2D, LIGHT, NKG2C, B7-H3, and any combination thereof.

In embodiments, the T cell-mediated immune response comprises the release of one or more cytokines comprising IFN-γ. In embodiments, the modified T cells comprise NK cells, T cells, natural killer T cells, cytotoxic T lymphocytes, and/or regulatory T cells.

In embodiments, the method further comprises administering an effective amount of a pharmaceutical composition comprising a population of modified cells comprising a CAR binding an antigen of a white blood cell (WBC). In embodiments, the WBC is a B cell. In embodiments, the antigen of the WBC is CD19, CD20, CD22, or BCMA.

Embodiments describe a bispecific CAR comprising a first antigen binding domain, a second antigen binding domain, a cytoplasmic domain, and transmembrane domain, wherein the first antigen binding domain recognizes a first antigen, and the second antigen binding domain recognizes a second antigen, and the first antigen is different from the second antigen. In embodiments, the first antigen and the second antigen are not expressed on the same cell. In embodiments, the first antigen is an antigen of a blood component, and the second antigen is an antigen of a solid tumor. In embodiments, the first antigen is CD19, and the second antigen is MAGE-A4 peptide.

In embodiments, the first binding domain binds an antigen of nonessential tissues, and the second binding domain binds an antigen of tumor tissue. For example, the first binding domain binds TSHR or GUCY2C, and the second binding domain binds MAGE-A4 peptide.

Embodiments describe a CAR, wherein the CAR comprises an extracellular domain, a transmembrane domain, and an intracellular domain, and wherein the extracellular domain comprises amino acid sequence SEQ ID NO: 10 or 13.

In embodiments, the CAR binds MAGE-A4 peptide. In embodiments, the CAR binds to MAGE-A4 peptide comprising amino acid sequence SED ID NO: 14. In embodiments, the CAR comprises amino acid sequence SED ID NO: 11 or 12. In embodiments, the CAR comprises amino acid sequence SED ID NO: 15, 16, or 17. In embodiments, the intracellular domain comprises a CD3 zeta signaling domain. In embodiments, the intracellular domain further comprises a co-stimulatory signaling region comprising an intracellular domain of a co-stimulatory molecule selected from the group consisting of CD27, CD28, 4-1BB (CD137), OX40, CD30, CD40, PD-1, ICOS, lymphocyte function-associated antigen-1 (LFA-1), CD2, CD7, CD40-MyD88, CD244, NKG2D, LIGHT, NKG2C, B7-H3, and any combination thereof.

Embodiments describe a composition comprising the CAR above and a carrier.

Embodiments describe a pharmaceutical composition comprising the CAR above and a pharmaceutically acceptable carrier. Embodiments describe a nucleic acid encoding the CAR above. Embodiments describe a vector comprising the nucleic acid encoding the CAR above. Embodiments describe a cell comprising the nucleic acid encoding the CAR above. Embodiments describe a population of cells comprising the nucleic acid encoding the CAR above. In embodiments, the population of cells comprises T cells. Embodiments describe a pharmaceutical composition comprising the population of T cells above.

Embodiments describe a method of stimulating an anti-tumor immune response in a subject in need thereof, the method comprising administering an effective amount of the pharmaceutical composition above to the subject, thereby stimulating an anti-tumor immune response. In embodiments, the subject is diagnosed with lung cancer, colon cancer, or bladder cancer. Embodiments describe a method of stimulating an immune response in a population of cells expressing MAGE-A4 peptide, the method comprising contacting the population of cells with an effective amount of the pharmaceutical composition above. In embodiments, the immune response is a T cell-mediated immune response. In embodiments, the population of cells is in a subject. In embodiments, the immune response is an anti-tumor immune response.

The present disclosure also describes one or more nucleic acids encoding a first CAR molecule and a second CAR molecule or a TCR. The first CAR includes the first antigen binding domain and the second CAR or TCR includes the second antigen binding domain. In embodiments, the first CAR and the second CAR or TCR are expressed as separate polypeptides and encoded by at least two separate nucleic acids. In embodiments, a single CAR contains at least the first and second antigen binding domains described herein and is encoded by a single nucleic acid. In embodiments, the two different antigen binding domains can be encoded by more than one nucleic acid. Moreover, the present disclosure describes vectors containing the nucleic acids described herein and cells comprising the nucleic acids described herein. In embodiments, the cells include genetically modified cells, for example, genetically modified T cells, such as CAR T cells.

The present disclosure also describes a population of modified cells, such as a mixed population of modified T cells, effective for expanding and/or maintaining the genetically modified cells in a patient. In embodiments, the mixed population of genetically modified cells includes at least two different genetically modified cells, a first genetically modified cell expressing an antigen binding domain for expanding and/or maintaining the modified cells and a second genetically modified cell expressing an antigen binding domain for killing a target cell, such as a tumor cell. The two antigen binding domains are different molecules and bind different antigens. In embodiments, the mixed population of genetically modified cells further includes a third genetically modified cell expressing at least two different antigen binding domains, a first antigen binding domain for expanding and/or maintaining the genetically modified cell and a second antigen binding domain for killing a target cell (wherein the two different antigen binding domains are expressed on the same cell).

In embodiments, the mixed population of modified cells includes genetically modified cells expressing at least two different antigen binding domains, a first antigen binding domain for expanding and/or maintaining the modified cells and a second antigen binding domain for killing a target cell (wherein the two different antigen binding domains are expressed on the same cell).

In embodiments, the mixed population of modified cells includes a modified cell expressing an antigen binding domain for killing a target cell and a modified cell expressing at least two antigen binding domains, a first antigen binding domain for expanding and/or maintaining the modified T cells and a second antigen binding domain for killing a target cell (wherein the two different antigen binding domains are expressed on the same modified cell).

In embodiments, the mixed population of modified cells includes a modified cell expressing an antigen binding domain for expanding and/or maintaining the modified T cells and a modified cell expressing at least two antigen binding domains, a first antigen binding domain for expanding and/or maintaining the modified cell and a second antigen binding domain for killing a target cell (wherein the two different antigen binding domains are expressed on the same modified cell).

The present disclosure describes compositions comprising the mixed population of modified cells described herein. More information about the mixed modified cells (e.g., T cells) and uses thereof can be found at PCT/US2020/13099, which is incorporated herein by its reference.

In embodiments, the modified cell is a modified T cell, a modified NK cell, a modified macrophage, or a modified dendritic cell. In embodiments, the modified T cell is a CAR T cell. In embodiments, the modified cell expressing two different antigen binding domains can be a single CAR T cell. In embodiments, the single CAR T cell can be a bispecific CAR T cell.

In embodiments, the antigen binding domain for expanding and/or maintaining the modified cell binds the surface antigen of a WBC, and the antigen binding domain for killing a target cell binds a tumor antigen. In embodiments, the WBC is a B cell. In embodiments, the surface antigen of a B cell is CD19, and the tumor antigen is MAGE-A4 peptide.

Furthermore, the present disclosure describes the use of the composition or the mixed population of modified cells described herein for enhancing the expansion and/or maintenance of CAR T cells in patients in need thereof. The enhanced expansion and maintenance of CAR T cells improve the efficacy of the CAR T cell therapy. The present disclosure describes a method of treating a patient having a tumor with a mixed population of modified cells described herein. In embodiments, the mixed population of genetically modified cells expands and/or maintains the modified cells in the patient and effectively inhibits the growth of the tumor. In embodiments, the tumor is a solid tumor.

Lymphocyte or T cell response in a subject refers to cell-mediated immunity associated with a helper, killer, regulatory, and other types of T cells. For example, T cell response may include activities such as assisting other WBCs in immunologic processes and identifying and destroying virus-infected cells and tumor cells. T cell response in the subject can be measured via various indicators such as the number of virus-infected cells and/or tumor cells that T cells kill, the amount of cytokines (e.g., IL-6 and IFN-γ) that T cells release in vivo and/or in co-culturing with virus-infected cells and/or tumor cells, indicates a level of proliferation of T cells in the subject, a phenotype change of T cells, for example, changes to memory T cells, and level longevity or lifetime of T cells in the subject.

In embodiments, the method of enhancing T cell response described herein can effectively treat a subject in need thereof, for example, a subject diagnosed with a tumor. The term tumor refers to a mass, which can be a collection of fluid, such as blood, or a solid mass. A tumor can be malignant (cancerous) or benign. Examples of blood cancers include chronic lymphocytic leukemia, acute myeloid leukemia, acute lymphoblastic leukemia, and multiple myeloma.

Solid tumors usually do not contain cysts or liquid areas. The major types of malignant solid tumors include sarcomas and carcinomas. Sarcomas are tumors that develop in soft tissue cells called mesenchymal cells, which can be found in blood vessels, bone, fat tissues, ligament lymph vessels, nerves, cartilage, muscle, ligaments, or tendon, while carcinomas are tumors that form in epithelial cells, which are found in the skin and mucous membranes. The most common types of sarcomas include undifferentiated pleomorphic sarcoma, which involves soft tissue and bone cells; leiomyosarcoma, which involves smooth muscle cells that line blood vessels, gastrointestinal tract, and uterus; osteosarcoma, which involves bone cells; and liposarcoma which involves fat cells. Some examples of sarcomas include Ewing sarcoma, Rhabdomyosarcoma, chondosarcoma, mesothelioma, fibrosarcoma, fibrosarcoma, and glioma.

The five most common carcinomas include adrenocarcinoma, which involves organs that produce fluids or mucous, such as the breasts and prostate; basal cell carcinoma, which involves cells of the outer-most layer of the skin, for example, skin cancer; squamous cell carcinoma, which involves the basal cells of the skin; and transitional cell carcinoma which affects transitional cells in the urinary tract which includes the bladder, kidneys, and ureter. Examples of carcinomas include cancers of the thyroid, breast, prostate, lung, intestine, skin, pancreas, liver, kidneys, and bladder, and cholangiocarcinoma.

The methods described herein can be used to treat a subject diagnosed with cancer. Cancer can be a blood cancer or can be a solid tumor, such as a sarcoma or carcinoma. The method of treating includes administering an effective amount of a mixed population of T cells described herein comprising a first antigen binding domain and/or a second antigen binding domain to the subject to provide a T-cell response, wherein the first antigen binding domain binds a cell surface molecule of a WBC, and the second antigen binding domain binds an antigen different from the cell surface molecule of the WBC. In embodiments, enhancing the T cell response in the subject includes selectively enhancing the proliferation of T cells expressing the first antigen binding domain and the second antigen binding domain in vivo.

Embodiments describe a modified cell comprising MAGE-A4 CAR and a dominant negative variant of a receptor of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), or CD 160. In embodiments, the modified cell further comprises a nucleic acid encoding a suicide gene, and/or the suicide gene comprises an HSV-TK suicide gene system. In embodiments, the isolated T cell comprises a reduced amount of TCR, as compared to the corresponding wide-type T cell.

Dominant negative mutations have an altered gene product that acts antagonistically to the wild-type allele. These mutations usually result in an altered molecular function (often inactive) and are characterized by a dominant or semi-dominant phenotype. In embodiments, the modified cells described herein comprise the dominant negative (DN) form of the PD-1 receptor. In embodiments, the expression of the DN PD-1 receptor in the modified cells described herein is regulated by an inducible gene expression system. In embodiments, the inducible gene expression system is a lac system, a tetracycline system, or a galactose system.

The present disclosure describes pharmaceutical compositions. The pharmaceutical compositions include one or more of the following: CAR molecules, TCR molecules, modified CAR T cells, modified cells comprising CAR or TCR, mix population of modified cells, nucleic acids, and vectors described herein. Pharmaceutical compositions are administered in a manner appropriate to the disease to be treated (or prevented). The quantity and frequency of administration will be determined by such factors as the condition of the patient, and the type and severity of the patient's disease, although appropriate dosages may be determined by clinical trials.

The term "pharmaceutically acceptable" means approved by a regulatory agency of the U.S. Federal or a state government or the EMA (European Medicines Agency) or listed in the U.S. Pharmacopeia (United States Pharmacopeia-33/National Formulary-28 Reissue, published by the United States Pharmacopeia Convention, Inc., Rockville Md., publication date: April 2010) or other generally recognized pharmacopeia for use in animals, and more particularly in humans.

The term "carrier" refers to a diluent, adjuvant {e.g., Freund's adjuvant (complete and incomplete)), excipient, or vehicle with which the therapeutic is administered. Pharmaceutical carriers can be sterile liquids, such as water and oils, including those of petroleum, animal, vegetable, or synthetic origins, such as peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly for injectable solutions.

When "an immunologically effective amount," "an anti-tumor effective amount," "a tumor-inhibiting effective amount," or "a therapeutically effective amount" is indicated, the precise amount of the compositions of the present disclosure to be administered can be determined by a physician with consideration of individual differences in age, weight, tumor size, the extent of infection or metastasis, and condition of the patient (subject). It can be stated that a pharmaceutical composition comprising the modified cells described herein may be administered at a dosage of $10^4$ to $10^9$ cells/kg body weight, preferably $10^5$ to $10^6$ cells/kg body weight, including all integer values within those ranges. Modified cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In embodiments, T cells can be activated from blood draws of from 10 cc to 400 cc. In embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols may select out certain populations of T cells.

The administration of the pharmaceutical compositions described herein may be carried out in any convenient manner, including by aerosol inhalation, injection, ingestion, transfusion, implantation, or transplantation. The compositions described herein may be administered to a patient subcutaneously, intradermally, intratumorally, intranodally, intramedullary, intramuscularly, by intravenous (i. v.) injection, or intraperitoneally. In embodiments, the modified cell compositions described herein are administered to subjects by intradermal or subcutaneous injection. In embodiments, the T cell compositions of the present disclosure are administered by i.v. injection. The compositions of modified cells may be injected directly into a tumor, lymph node, or site of infection. In embodiments, cells activated and expanded using the methods described herein, or other methods known in the art where T cells are expanded to therapeutic levels, are administered to patients in conjunction with (e.g., before, simultaneously, or following) any number of relevant treatment modalities, for example as a combination therapy, including but not limited to treatment with agents for antiviral therapy, cidofovir, and interleukin-2, Cytarabine (also known as ARA-C); or natalizumab treatment for MS patients; or efalizumab treatment for psoriasis patients or other treatments for PML patients. In further embodiments, the T cells described herein can be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies, or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions described herein are administered to a subject in conjunction with (e.g., before, simultaneously, or following) bone marrow transplantation, T cell ablative therapy using either chemotherapy agents such as fludarabine, external-beam radiation therapy (XRT), cyclophosphamide, or antibodies such as OKT3 or CAM-PATH. In embodiments, the cell compositions described herein are administered following B-cell ablative therapy. For example, agents that react with CD20, e.g., Rituxan, may be administered to patients. In embodiments, subjects may undergo standard treatment with high dose chemotherapy followed by peripheral blood stem cell transplantation. In embodiments, following the transplant, subjects receive an infusion of the expanded immune cells of the present disclosure. In embodiments, expanded cells are administered before or following surgery. The dosage of the above treatments to be administered to a subject in need thereof will vary with the precise nature of the condition being treated and the recipient of the treatment. The scaling of dosages for human administration can be performed according to art-accepted practices by a physician, depending on various factors. Additional information on the methods of cancer treatment using modified cells is provided in U.S. Pat. No. 8,906,682, incorporated by reference in its entirety.

In embodiments, T cell response in a subject refers to cell-mediated immunity associated with helper, killer, regulatory, and other types of T cells. For example, T cell response may include activities such as assistance to other white blood cells in immunologic processes and identifying and destroying virus-infected cells and tumor cells. T cell response in the subject may be measured via various indicators such as a number of virus-infected cells and/or tumor cells that the T cells kill, an amount of cytokines that the T cells release in co-culturing with virus-infected cells and/or tumor cells, a level of proliferation of the T cells in the subject, a phenotype change of the T cells (e.g., changes to memory T cells), and the longevity or the length of the lifetime of the T cells in the subject.

T cell response also includes the release of cytokines. Although cytokine release is often associated with systemic inflammation and complication of the disease, the release of cytokines appears to be also associated with the efficacy of a CAR T cell therapy. The release of cytokines may correlate with expansion and progressive immune activation of adoptively transferred cells, such as in CAR T cell therapy. The present disclosure describes the release of effector cytokines, such as IFN-γ, and pro-inflammatory and anti-inflammatory cytokines, such as IL-6, in response to a mixed population of modified T cells described herein, especially in response to the presence of a first CAR including an antigen binding domain for expanding cells and a second CAR or TCR including an antigen binding domain for killing a target cell. In embodiments, the present disclosure describes the release of IL-6 and IFN-γ in a subject introduced with the first CAR and second CAR or TCR described herein. In embodiments, the subject is in need of cancer treatment, and the cancer treatment is pancreatic cancer treatment. In embodiments, the present disclosure describes determining the efficacy or monitoring the efficacy of a CAR T cell therapy by measuring the level of cytokine release. In embodiments, the release of cytokines (e.g., IL-6 and/or IFN-γ) in the subject in response to CAR T cell therapy using a mixed population of modified T cells described herein is more than that using T cells comprising the second CAR without the first CAR.

Embodiments relate to a method of using or use of a polynucleotide encoding MAGE-A4 CAR and/or therapeutic agent(s) to treat a subject having cancer (e.g., lung cancer). In embodiments, the method or use includes providing a viral particle (e.g., AAV, lentivirus, or their variants) comprising a vector genome, the vector genome comprising the polynucleotide, wherein the polynucleotide is operably linked to an expression control element conferring transcription of the polynucleotide and administering an amount of the viral particle to the subject such that the polynucleotide is expressed in the subject. In embodiments, the AAV preparation may include AAV vector particles, empty capsids, and host cell impurities, thereby providing an AAV product substantially free of AAV empty capsids. More information on the administration and preparation of the viral particle may be found at the U.S. Pat. No. 9,840,719 and Milani et al., Sci. Transl. Med. 11, eaav7325 (2019) 22 May 2019, which are incorporated herein by reference.

In embodiments, the polynucleotide may integrate into the genome of the modified cell, and the progeny of the modified cell will also express the polynucleotide, resulting in a stably transfected modified cell. In embodiments, the modified cell expresses the polynucleotide encoding the CAR, but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

In embodiments, the therapeutic agent comprises or is a cytokine. Examples of the cytokine include IL-1P, IL-2, IL-4, IL-5, IL-6, IL-8, IL-10, IL-12, IL-13, IL-15, IL-17, IL-1Ra, IL-2R, IFN-γ, MIP-In, MIP-IP, MCP-1, TNFα, GM-CSF, GCSF, CXCL9, CXCL10, CXCR factors, VEGF, RANTES, EOTAXIN, EGF, HGF, FGF-P, CD40, CD40L, ferritin, and any combination thereof. In embodiments, the cytokines include proinflammatory cytokines such as IFN-γ, IL-15, IL-4, IL-10, TNFα, IL-8, IL-5, IL-6, GM-CSF, and MIP-lα. In embodiments, the viral particles include multiple polynucleotides, and a polynucleotide encodes at least one of IFN-γ, IL-2, IL-6, IL-7, IL-15, IL-17, IL-12, and IL-23. More information about the therapeutic agent and the use thereof can be found in PCT Publication NO: WO2020106843, which is incorporated by its entity.

The following are exemplary embodiments:

1. Lymphocytes for use in a method of treating a subject having a solid tumor expressing MAGE-A4 peptide or stimulating a T cell-mediated immune response in the subject, the method comprising: administering an effective amount of lymphocytes to the subject having the solid tumor; wherein the lymphocytes comprise a CAR comprising an extracellular domain, a transmembrane domain, and an intracellular domain, and wherein the extracellular domain comprises amino acid sequence SEQ ID NO: 10 or 13.

2. The Lymphocytes of embodiment 1, wherein the CAR binds Melanoma-associated antigen 4 (MAGE-A4) peptide.

3. The Lymphocytes of embodiment 1, wherein the CAR binds to MAGE-A4 peptide comprising amino acid sequence SED ID NO: 14.

4. The Lymphocytes of embodiment 1, wherein the CAR comprises amino acid sequence SED ID NO: 11 or 12.

5. The Lymphocytes of embodiment 1, wherein the CAR comprises amino acid sequence SED ID NO: 16, or 17.

6. The Lymphocytes of embodiment 1, wherein the intracellular domain comprises one or more signaling domains of CD3 zeta, DAP10, DAP12, FcεRIγ, Fyn, Lck, Syk, and Zap70.

7. The Lymphocytes of embodiment 1, wherein the intracellular domain further comprises a co-stimulatory signaling region comprising an intracellular domain of a co-stimulatory molecule selected from the group consisting of CD27, CD28, 4-1BB (CD137), OX40, CD30, CD40, PD-1, ICOS, lymphocyte function-associated antigen-1 (LFA-1), CD2, CD7, CD40-MyD88, CD244, NKG2D, LIGHT, NKG2C, B7-H3, and any combination thereof.

8. Lymphocytes for use in a method of treating a subject having a solid tumor expressing MAGE-A4 peptide or stimulating a T cell-mediated immune response in the subject, the method comprising: administering an effective amount of lymphocytes to the subject having the solid tumor; wherein the lymphocytes comprise a CAR binding MAGE-A4 peptide comprising the amino acid sequence of SEQ ID NO: 14, and the CAR comprises an extracellular domain, a transmembrane domain, and an intracellular domain, the extracellular domain comprising the amino acid sequences SEQ ID NO: 8 and SEQ ID NO: 9.

9. The Lymphocytes of embodiment 8, wherein the intracellular domain comprises one or more signaling domains of CD3 zeta, DAP10, DAP12, FcεRIγ, Fyn, Lck, Syk, and Zap70.

10. The Lymphocytes of embodiment 8, wherein the intracellular domain further comprises a co-stimulatory signaling region comprising an intracellular domain of a co-stimulatory molecule selected from the group consisting of CD27, CD28, 4-1BB (CD137), OX40, CD30, CD40, PD-1, ICOS, lymphocyte function-associated antigen-1 (LFA-1), CD2, CD7, CD40-MyD88, CD244, NKG2D, LIGHT, NKG2C, B7-H3, and any combination thereof.

11. The Lymphocytes of embodiment 8, wherein the T cell-mediated immune response comprises the release of one or more cytokines comprising IFN-γ.

12. The Lymphocytes of embodiment 8, wherein the modified T cells comprise NK cells, T cells, natural killer T cells, cytotoxic T lymphocytes, and/or regulatory T cells.

13. The Lymphocytes of any one of embodiments 1-12, wherein the method further comprises administering an effective amount of a pharmaceutical composition comprising a population of modified cells comprising a CAR binding an antigen of a WBC.

14. The method of embodiment 13, wherein the WBC is a B cell.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples but rather should be construed to encompass any and all variations which become evident as a result of the teaching provided herein.

EXAMPLES

Lentiviral vectors that encode individual CAR molecules were generated and transfected into T cells, which are described below. Techniques related to cell cultures, construction of cytotoxic T lymphocyte assay can be found in "Control of large, established tumor xenografts with genetically retargeted human T cells containing CD28 and CD137 domains," PNAS, Mar. 3, 2009, vol. 106 no. 9, 3360-3365 and "Chimeric Receptors Containing CD137 Signal Transduction Domains Mediate Enhanced Survival of T Cells and Increased Antileukemic Efficacy In Vivo," Molecular Therapy, August. 2009, vol. 17 no. 8, 1453-1464, which are incorporated herein by reference in their entirety.

FIG. 1 shows flow cytometry results of the expression of CAR and CD137 on T cells. On day 0, peripheral blood was drawn from healthy volunteers and sorted to collect $CD3^+$ T cells. Anti-CD3/CD28 dynabeads were added to the collected T cells at a 1:1 ratio. On day 1, the activated T cells were mixed with various vectors encoding CARs binding CD19 (CD19 CAR) (multiplicity of infection (MOI)=15) (SEQ ID NO: 5) and vectors encoding CARs binding MAGE-A4 peptide (MAGE-A4 CAR) (MOI=15) (SEQ ID NO: 10).

Figure 2:
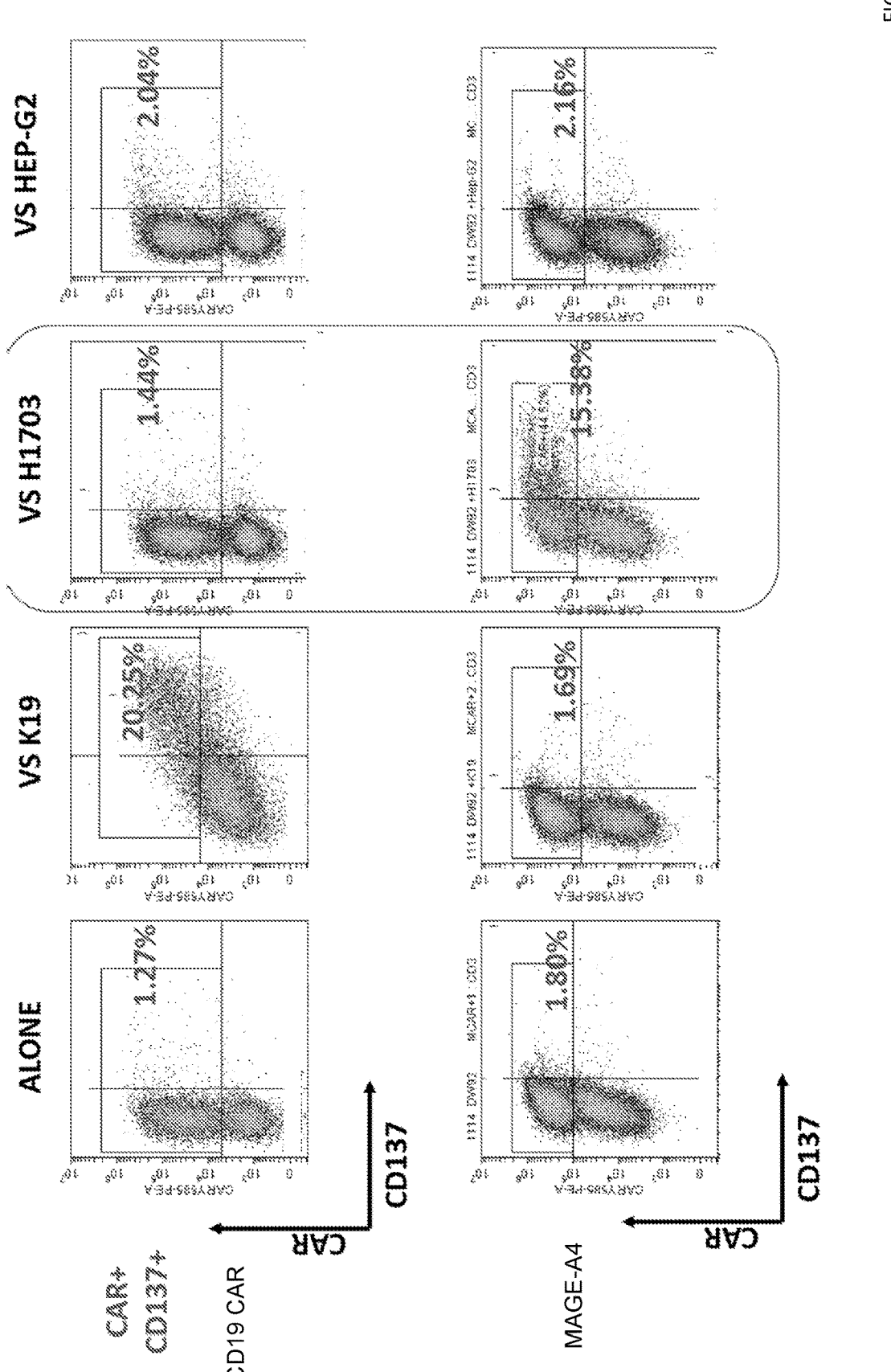
FIG. 2 shows flow cytometry results of the expression of CD137 on CAR T cells co-cultured with substrate cells for 24 hours.
Figure 3B:
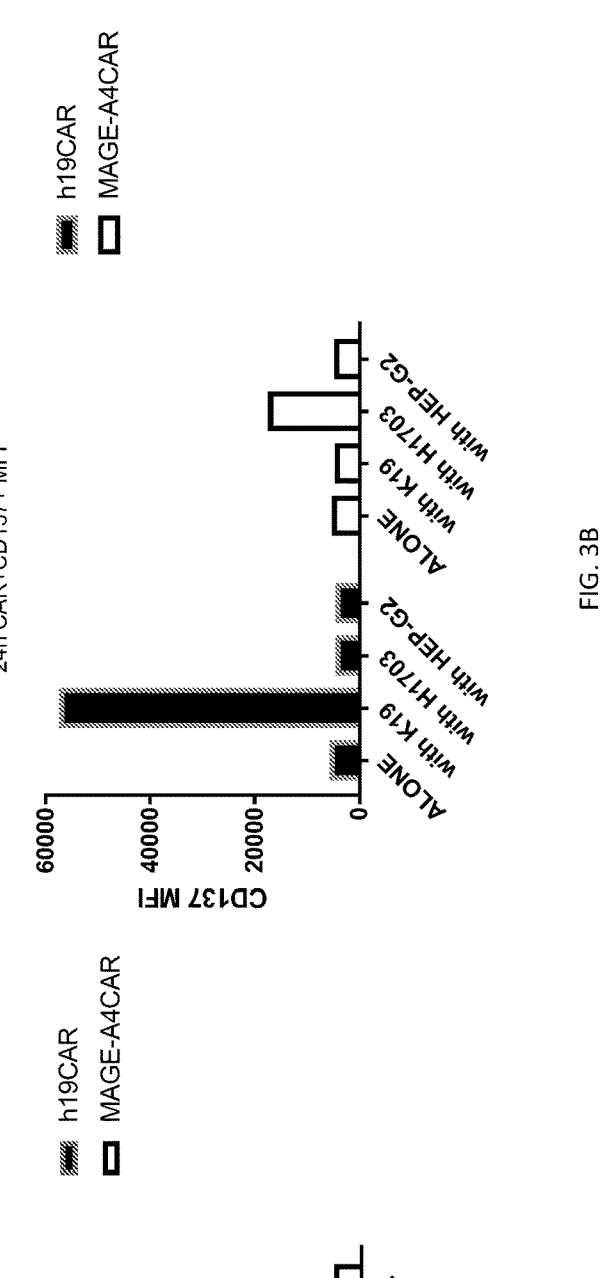
FIGS. 3A and 3B show flow cytometry results of FIG. 2 in histograms.
Figure 3A:
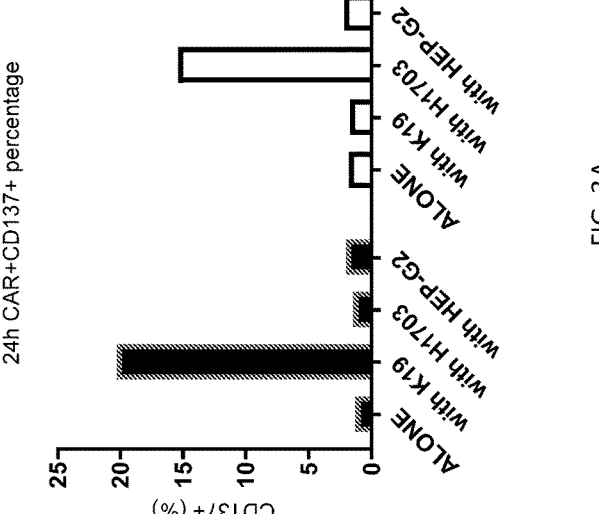
Figure 4B:
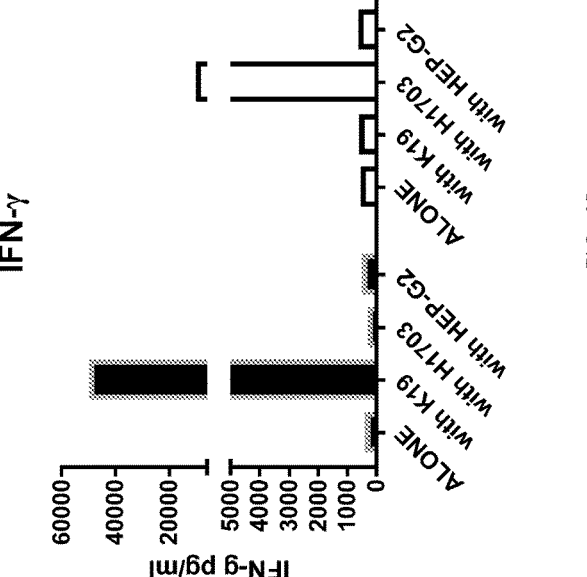
FIGS. 4A and 4B show cytokine release of CAR T cells co-cultured with substrate cells for 24 hours.
Figure 4A:
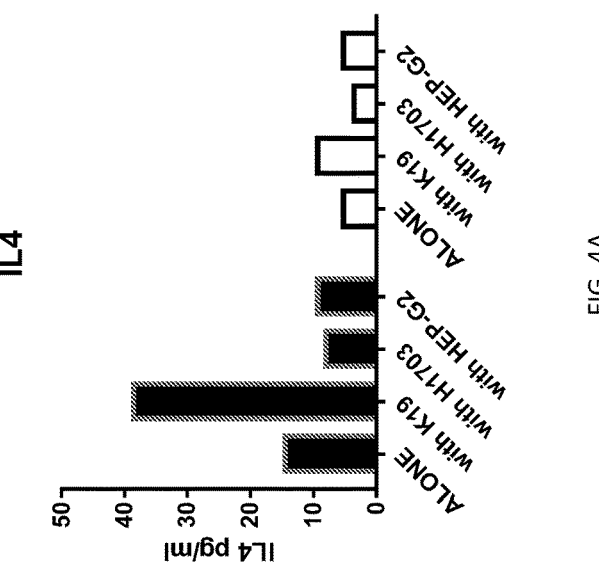

FIG. 2 shows flow cytometry results of the expression of CD137 on CAR T cells co-cultured with substrate cells for 24 hours. H1703 is a classic $HLA-02^+$ and MAGE-A4 $peptide^+$ tumor cell, K19 is a $CD19^+$ cell, and HEP-G2 is a MAGE-A4$^{--}$ cell. As shown in FIG. 2, expression CD137 of MAGE-A4 CAR increased, indicating MAGE-A4 CAR T cells were activated when co-cultured with H1703. FIG. 3 shows flow cytometry results of FIG. 2 in histograms. FIG. 4 shows cytokine release of CAR T cells co-cultured with substrate cells for 24 hours. As shown in FIG. 4, co-culturing with H1703 caused MAGE-A4 CAR T cells to release cytokines (IL4 and IFN-γ).

Figure 5B:
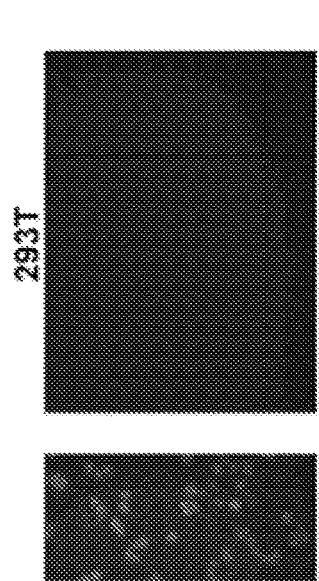
FIGS. 5A, 5B, and 5C show the anti-tumor effect of MAGE-A4 CAR T cells in in vitro experiment.
Figure 5A:
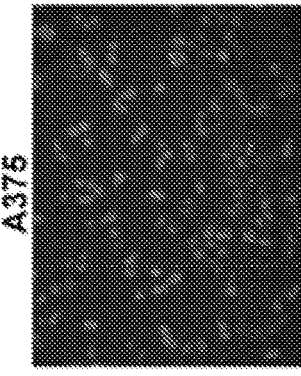
Figure 5C:
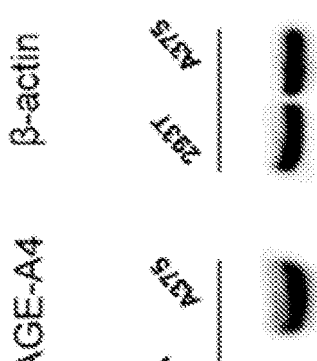
Figure 5C:
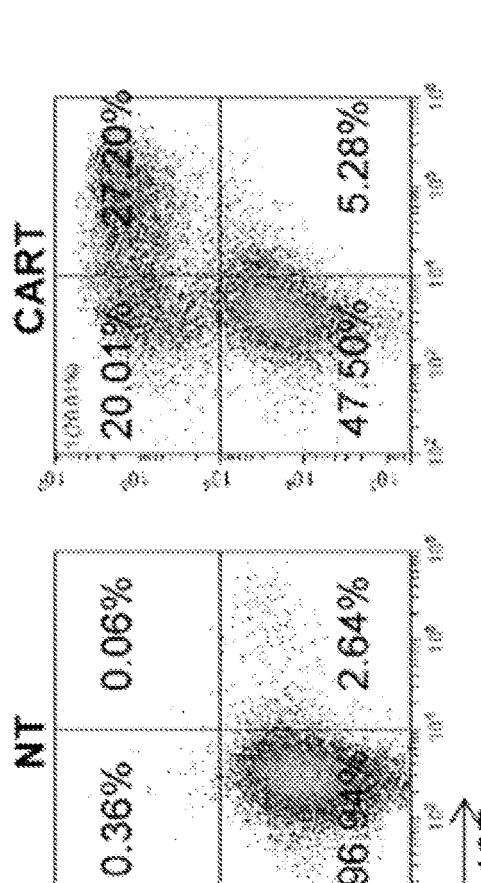
Figure 5C:
Figures 6A, 6B:
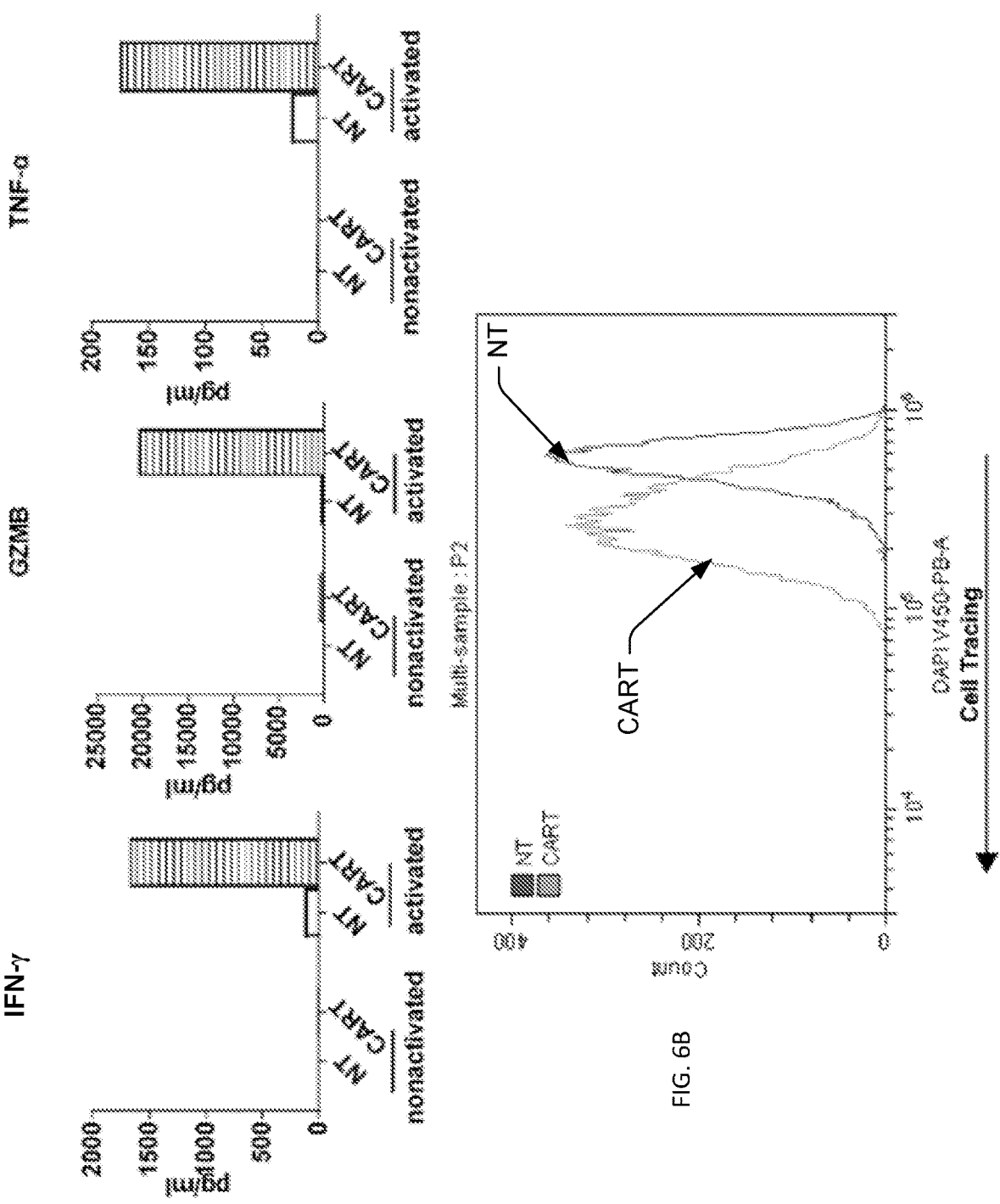
FIGS. 6A and 6B show cytokine release and cell expansion of MAGE-A4 CAR T cells co-cultured with substrate cells.

FIGS. 5A-5C show the anti-tumor effect of MAGE-A4 CAR T cells in in vitro experiment. FIG. 5A shows the expression of MAGE-A4 in human embryonic kidney (HEK) cell line 293T and human tumor cell line A375 with Western Blot. FIG. 5B shows the expression of MAGE-A4 in cell line 293T and A375 with Immunofluorescence (IF) staining. FIG. 5C shows expression of CD137 in MAGE-A4 CAR T cells co-cultured with the A375 cell lines. FIGS. 6A and 6B show cytokine release and cell expansion of MAGE-A4 CAR T cells co-cultured with substrate cells. FIG. 6A shows the release of cytokines including TNF-α, IFN-γ, and Gramzyme B. FIG. 6B shows the expansion of MAGE-A4 CAR T cells analyzed using CellTracing™.

NOD scid gamma (NPG™) mice were introduced with a tumor model by subcutaneous injection of $4.0×10^6$ A375 cells. Mice implanted with tumor cells were randomly divided into three groups, namely the Mock group (n=3), NT group (n=4), CAR T group (n=4). They were given PBS, $3.0×10^6$ NT cells, or $3.0×10^6$ MAGE-A4 CAR T cells through the caudal vein, respectively. The mice were monitored, and blood was taken from the retro-orbital sinus to detect the proliferation and cytokine release of T cells in peripheral blood. Eventually, the mice were sacrificed, and tumor sizes were measured.

Figures 7A, 7B, 7C:
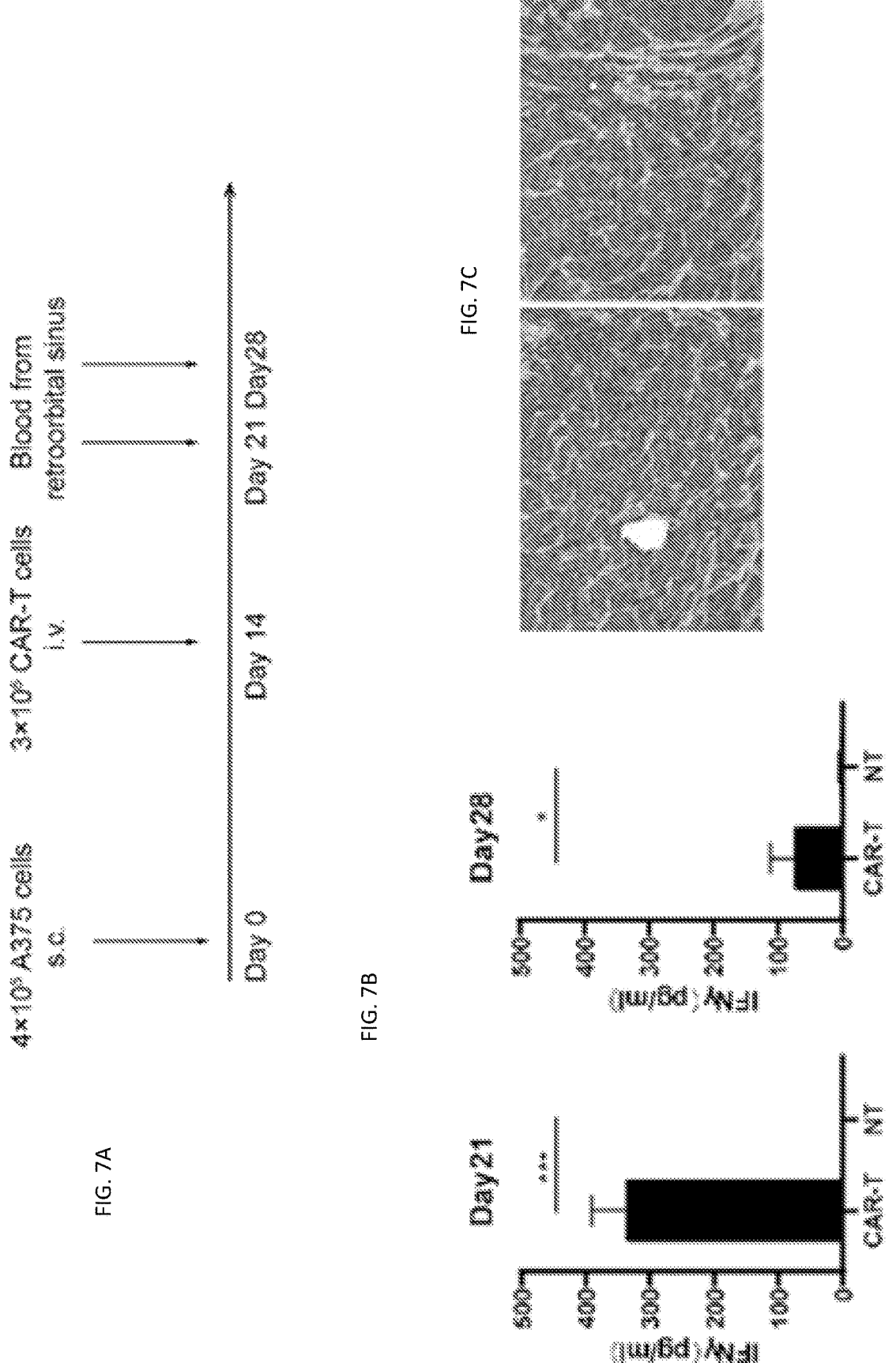
FIGS. 7A, 7B, and 7C show a schematic of the in vivo experimental protocol and the results of the in vivo experiment demonstrating that MAGE-A4 CAR T has anti-tumor activities.
Figure 8:
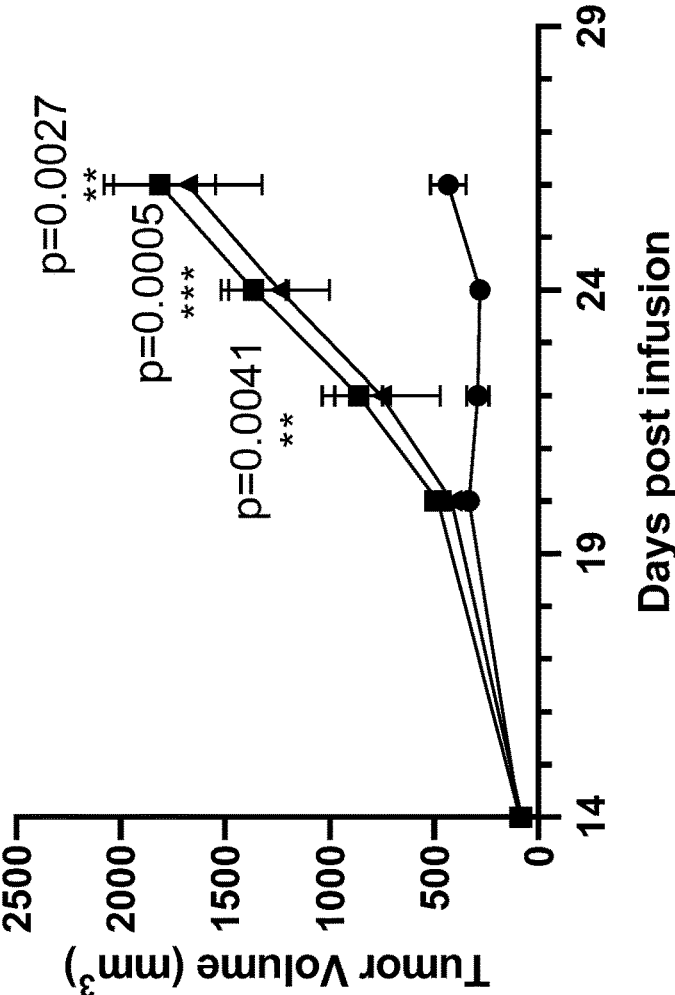
FIG. 8 shows changes in the volumes of the tumors in the mice of the experiment shown in FIG. 7.

FIGS. 7A-7C show a schematic of the in vivo experimental protocol and the results of the in vivo experiment demonstrating that MAGE-A4 CAR T has anti-tumor activities. FIG. 7A shows the in vivo experimental protocol. FIG. 7B shows cytokine release of IFN-γ in peripheral blood of mice on day 21 and day 28. FIG. 7C shows the expression of MAGE-A4 in mice detected by immunohistochemical (IHC) staining. (Antibody: CST, Inc. MAGE-A4 (E701U) XP Rabbit mAb #824910). FIG. 8 shows changes in the volumes of the tumor in mice of experiment of FIG. 7($*P<0.05$, $P<0.01$, $*P<0.001$, and ns means no significant difference).

Figures 9A, 9B:
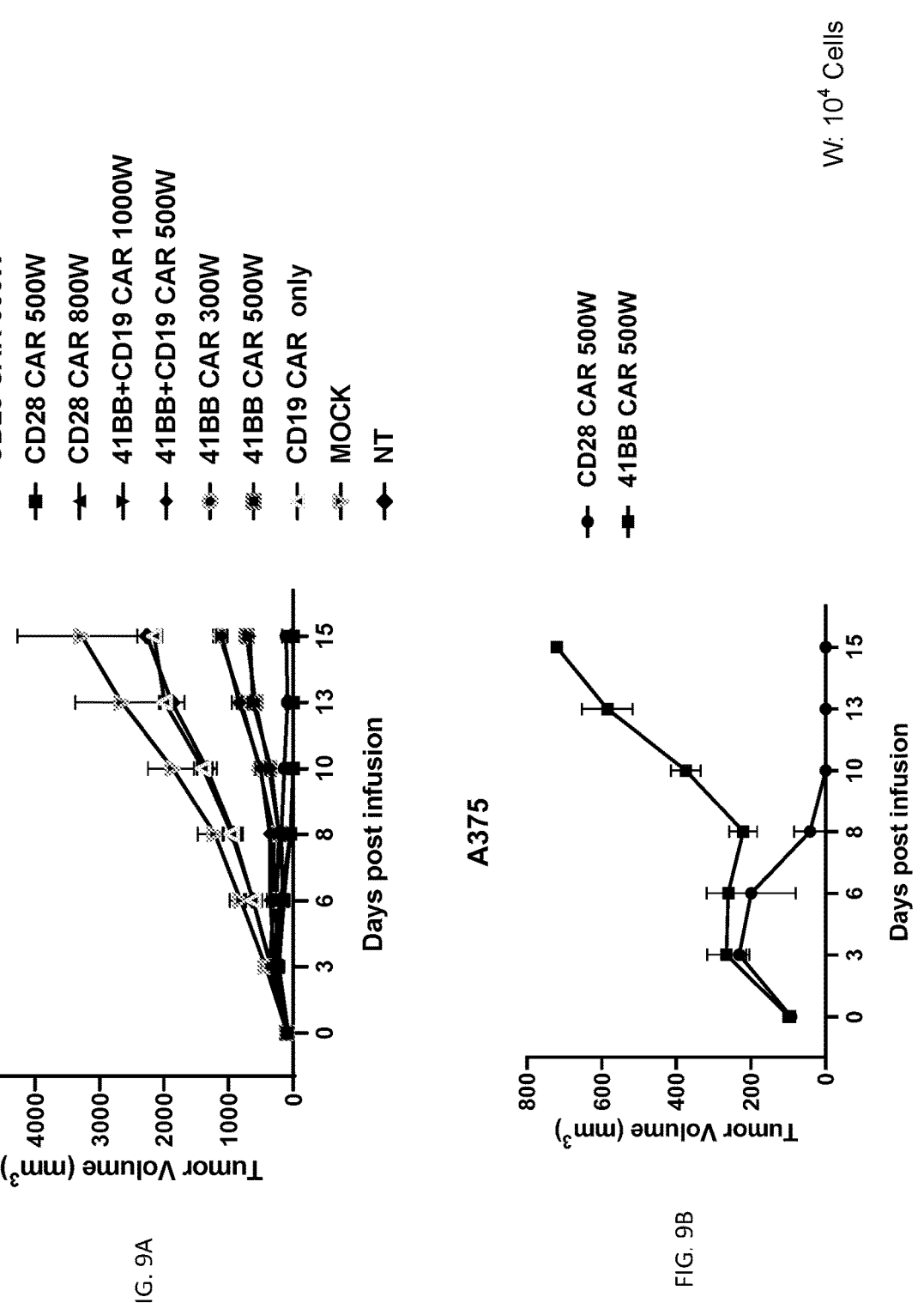
FIGS. 9A and 9B show comparisons of antitumor activities between MAGE-A4 CARs, including the co-stimulatory domain of 4-1BB (MAGE-A4 4-1 BB CAR) or CD28 (MAGE-A4 CD28 CAR).

FIGS. 9A and 9B show comparisons of antitumor activities of MAGE-A4 CARs, including co-stimulatory domains of 4-1BB (MAGE-A4 4-1BB CAR) and CD28 (MAGE-A4 CD28 CAR). NPG™ mice were introduced with a tumor by subcutaneous injection of $4.0×10^6$ A375 cells. The mice implanted with tumor cells were randomly divided into three groups, namely the Mock group (n=3), NT group (n=4), CAR T group (n=4). They were given MAGE-A4 4-1BB CAR T cells or MAGE-A4 CD28 CAR T cells through the caudal vein, respectively. The mice were monitored, and blood was taken from the retro-orbital sinus to detect the proliferation and cytokine release of T cells in the peripheral blood. Eventually, the mice were sacrificed, and the size of their tumors was measured. The results showed that MAGE-A4 CD28 CAR T cells showed stronger anti-tumor activities than MAGE-A4 4-1BB CAR T cells.

TABLE 2

Sequence IDs and corresponding identifiers

| Name | SEQ ID: |
|---|---|
| SP | 1 |
| Hinge & transmembrane domain | 2 |
| Co-stimulatory domain | 3 |
| CD3-zeta | 4 |
| scFv Humanized CD19 | 5 |
| scFv CD19 | 6 |
| WTCD3zeta | 7 |
| MAGE-A4 VL chain | 8 |
| MAGE-A4 VH chain | 9 |
| MAGE-A4 scFv 1 | 10 |
| MAGE-A4 CAR 1 (41BB) | 11 |
| MAGE-A4 CAR 2 (CD28) | 12 |
| MAGE-A4 scFv 2 | 13 |
| MAGE-A4 peptide | 14 |
| MAGE-A4 CAR 3 | 15 |
| MAGE-A4 CAR 4 | 16 |
| MAGE-A4 CAR 5 | 17 |

All publications, patents, and patent applications cited in this specification are incorporated herein by reference in their entirety as if each individual publication, patent, or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A chimeric antigen receptor (CAR), wherein the CAR comprises an extracellular domain, a transmembrane domain, and an intracellular domain, wherein the extracellular domain comprises amino acid sequence SEQ ID NO: 10 or 13, and wherein the intracellular domain comprises a CD3 zeta signaling domain and a co-stimulatory signaling domain comprising an intracellular domain of CD28 or 4-1 BB.

2. The CAR of claim 1, wherein the CAR binds a human melanoma-associated antigen 4 (MAGE-A4) peptide.

3. The CAR of claim 1, wherein the CAR binds a MAGE-A4 peptide comprising amino acid sequence SED ID NO: 14.

4. The CAR of claim 1, wherein the CAR comprises amino acid sequence SED ID NO: 11 or 12.

5. The CAR of claim 1, wherein the CAR comprises amino acid sequence SED ID NO: 16, or 17.

6. A composition comprising the CAR of claim 1 and a carrier.

7. A pharmaceutical composition comprising the CAR of claim 1 and a pharmaceutically acceptable carrier.

8. A nucleic acid encoding the CAR of claim 1.

9. A vector comprising a nucleic acid encoding the CAR of claim 8.

10. A cell comprising a nucleic acid encoding the CAR of claim 1.

11. A population of cells comprising a nucleic acid encoding the CAR of claim 1.

12. The population of cells of claim 11, wherein the population of cells comprises T cells and/or NK cells.

13. A pharmaceutical composition comprising the population of T cells of claim 12.

14. A method of stimulating an anti-tumor immune response in a human subject in need thereof, the method comprising administering an effective amount of the pharmaceutical composition of claim 13 to the human subject, thereby stimulating an anti-tumor immune response.

15. The method of claim 14, wherein the human subject is diagnosed with lung cancer, colon cancer, or bladder cancer.

16. A method of stimulating an immune response in a population of cells expressing MAGE-A4 peptide, the method comprising contacting the population of cells with an effective amount of the pharmaceutical composition of claim 13.

17. The method of claim 16, wherein the immune response is a T cell-mediated immune response.

18. The method of claim 16, wherein the population of cells is in a human subject.

19. The method of claim 16, wherein the immune response is an anti-tumor immune response.

20. The CAR of claim 1, wherein the transmembrane domain comprises a transmembrane domain of CD8a or CD28.

* * * * *

SEQUENCE LISTING

```
<160> NUMBER OF SEQ ID NOS: 18

<210> SEQ ID NO 1
<211> LENGTH: 21
<212> TYPE: PRT
<213> ORGANISM: Homo sapiens

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 69
<212> TYPE: PRT
<213> ORGANISM: Homo sapiens

<400> SEQUENCE: 2

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65

<210> SEQ ID NO 3
<211> LENGTH: 42
<212> TYPE: PRT
<213> ORGANISM: Homo sapiens

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 4
<211> LENGTH: 112
<212> TYPE: PRT
<213> ORGANISM: Homo sapiens

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
```

```
              50               55               60

Asp Lys Met Ala Glu Ala Tyr Ser Glu Ile Gly Met Lys Gly Glu Arg
65               70               75               80

Arg Arg Gly Lys Gly His Asp Gly Leu Tyr Gln Gly Leu Ser Thr Ala
                85               90               95

Thr Lys Asp Thr Tyr Asp Ala Leu His Met Gln Ala Leu Pro Pro Arg
            100              105              110

<210> SEQ ID NO 5
<211> LENGTH: 242
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5               10               15

Asp Arg Val Thr Ile Thr Cys Arg Ala Ser Gln Asp Ile Ser Lys Tyr
                20               25               30

Leu Asn Trp Tyr Gln Gln Lys Pro Gly Lys Ala Pro Lys Leu Leu Ile
            35               40               45

Tyr His Thr Ser Arg Leu His Ser Gly Val Pro Ser Arg Phe Ser Gly
    50               55               60

Ser Gly Ser Gly Thr Asp Phe Thr Leu Thr Ile Ser Ser Leu Gln Pro
65               70               75               80

Glu Asp Phe Ala Thr Tyr Tyr Cys Gln Gln Gly Asn Thr Leu Pro Tyr
                85               90               95

Thr Phe Gly Gln Gly Thr Lys Val Glu Ile Lys Gly Gly Gly Gly Ser
            100              105              110

Gly Gly Gly Gly Ser Gly Gly Gly Ser Glu Val Gln Leu Val Glu
            115              120              125

Ser Gly Gly Gly Leu Val Gln Pro Gly Gly Ser Leu Arg Leu Ser Cys
    130              135              140

Ala Ala Ser Gly Val Ser Leu Pro Asp Tyr Gly Val Ser Trp Val Arg
145              150              155              160

Gln Ala Pro Gly Lys Gly Leu Glu Trp Val Ser Val Ile Trp Gly Ser
                165              170              175

Glu Thr Thr Tyr Tyr Asn Ser Ala Leu Lys Ser Arg Phe Thr Ile Ser
            180              185              190

Arg Asp Asn Ala Lys Asn Ser Leu Tyr Leu Gln Met Asn Ser Leu Arg
            195              200              205

Ala Glu Asp Thr Ala Val Tyr Tyr Cys Ala Lys His Tyr Tyr Tyr Gly
    210              215              220

Gly Ser Tyr Ala Met Asp Tyr Trp Gly Gln Gly Thr Leu Val Thr Val
225              230              235              240

Ser Ser

<210> SEQ ID NO 6
<211> LENGTH: 242
<212> TYPE: PRT
<213> ORGANISM: Homo sapiens

<400> SEQUENCE: 6

Asp Ile Gln Met Thr Gln Thr Thr Ser Ser Leu Ser Ala Ser Leu Gly
1               5               10               15

Asp Arg Val Thr Ile Ser Cys Arg Ala Ser Gln Asp Ile Ser Lys Tyr
                20               25               30
```

-continued

```
Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 7
<211> LENGTH: 244
<212> TYPE: PRT
<213> ORGANISM: Homo sapiens

<400> SEQUENCE: 7

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Gly Ser Gly Gly Gly Gly Ser Glu Val Gln
            115                 120                 125

Leu Val Gln Ser Gly Ala Glu Val Lys Lys Pro Gly Gln Ser Leu Lys
        130                 135                 140

Ile Ser Cys Lys Ala Ser Gly Tyr Ser Leu Thr Asp Asn Trp Ile Gly
145                 150                 155                 160
```

Trp Val Arg Gln Lys Pro Gly Lys Gly Leu Glu Trp Met Gly Ile Ile
              165             170             175

Tyr Pro Gly Asp Ser Asp Thr Arg Tyr Ser Pro Ser Phe Gln Gly Gln
              180             185             190

Val Thr Ile Ser Ala Asp Lys Ser Ile Asn Thr Ala Tyr Leu Gln Trp
              195             200             205

Ser Ser Leu Lys Ala Ser Asp Thr Ala Ile Tyr Tyr Cys Val Gly Leu
              210             215             220

Asp Trp Asn Tyr Asn Pro Leu Arg Tyr Trp Gly Pro Gly Thr Leu Val
225                 230             235             240

Thr Val Ser Ser

<210> SEQ ID NO 8
<211> LENGTH: 106
<212> TYPE: PRT
<213> ORGANISM: Homo sapiens

<400> SEQUENCE: 8

Gln Ile Val Leu Thr Gln Ser Pro Ala Ile Met Ser Ala Ser Pro Gly
1               5               10              15

Glu Lys Val Thr Ile Thr Cys Ser Val Ser Ser Ser Val Asp Tyr Ile
              20              25              30

His Trp Phe Gln Gln Lys Pro Gly Thr Ser Pro Lys Phe Trp Ile Tyr
              35              40              45

Ser Thr Ser Ile Leu Ala Ser Gly Val Pro Ala Arg Phe Ser Gly Ser
              50              55              60

Gly Ser Gly Thr Ser Tyr Ser Leu Thr Ile Ser Arg Met Glu Ala Glu
65              70              75              80

Asp Ala Ala Thr Tyr Tyr Cys Gln Gln Arg Ser Ser Tyr Pro Pro Thr
                  85              90              95

Phe Gly Ser Gly Thr Lys Leu Glu Ile Lys
              100             105

<210> SEQ ID NO 9
<211> LENGTH: 116
<212> TYPE: PRT
<213> ORGANISM: Homo sapiens

<400> SEQUENCE: 9

Gln Val Gln Leu Gln Gln Ser Gly Gly Glu Val Met Lys Pro Gly Ala
1               5               10              15

Ser Val Lys Leu Ser Cys Lys Ala Thr Gly Tyr Thr Phe Thr Gly Tyr
              20              25              30

Trp Ile Glu Trp Ile Lys Gln Arg Pro Gly His Gly Leu Glu Trp Ile
              35              40              45

Gly Glu Ile Leu Pro Gly Ser Gly Gly Thr Asn Tyr Asn Glu Lys Phe
              50              55              60

Lys Gly Lys Ala Thr Phe Thr Ala His Thr Ser Ser Asn Thr Ala Tyr
65                  70              75              80

Met Gln Leu Ser Ser Leu Thr Thr Glu Asp Ser Ala Ile Tyr Tyr Cys
                  85              90              95

Ala Arg Asp Ser Asn Ser Phe Thr Tyr Trp Gly Gln Gly Thr Leu Val
              100             105             110

Thr Val Ser Ser
              115

-continued

```
<210> SEQ ID NO 10
<211> LENGTH: 237
<212> TYPE: PRT
<213> ORGANISM: Homo sapiens

<400> SEQUENCE: 10

Gln Ile Val Leu Thr Gln Ser Pro Ala Ile Met Ser Ala Ser Pro Gly
1               5                   10                  15

Glu Lys Val Thr Ile Thr Cys Ser Val Ser Ser Ser Val Asp Tyr Ile
            20                  25                  30

His Trp Phe Gln Gln Lys Pro Gly Thr Ser Pro Lys Phe Trp Ile Tyr
        35                  40                  45

Ser Thr Ser Ile Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Ser Gly Thr Lys Leu Glu Ile Lys Gly Gly Gly Gly Ser Gly
            100                 105                 110

Gly Gly Gly Ser Gly Gly Gly Ser Gln Val Gln Leu Gln Gln Ser
        115                 120                 125

Gly Gly Glu Val Met Lys Pro Gly Ala Ser Val Lys Leu Ser Cys Lys
    130                 135                 140

Ala Thr Gly Tyr Thr Phe Thr Gly Tyr Trp Ile Glu Trp Ile Lys Gln
145                 150                 155                 160

Arg Pro Gly His Gly Leu Glu Trp Ile Gly Glu Ile Leu Pro Gly Ser
                165                 170                 175

Gly Gly Thr Asn Tyr Asn Glu Lys Phe Lys Gly Lys Ala Thr Phe Thr
                180                 185                 190

Ala His Thr Ser Ser Asn Thr Ala Tyr Met Gln Leu Ser Ser Leu Thr
            195                 200                 205

Thr Glu Asp Ser Ala Ile Tyr Tyr Cys Ala Arg Asp Ser Asn Ser Phe
    210                 215                 220

Thr Tyr Trp Gly Gln Gly Thr Leu Val Thr Val Ser Ser
225                 230                 235

<210> SEQ ID NO 11
<211> LENGTH: 481
<212> TYPE: PRT
<213> ORGANISM: Homo sapiens

<400> SEQUENCE: 11

Met Ala Leu Pro Val Thr Ala Leu Leu Leu Pro Leu Ala Leu Leu Leu
1               5                   10                  15

His Ala Ala Arg Pro Gln Ile Val Leu Thr Gln Ser Pro Ala Ile Met
            20                  25                  30

Ser Ala Ser Pro Gly Glu Lys Val Thr Ile Thr Cys Ser Val Ser Ser
        35                  40                  45

Ser Val Asp Tyr Ile His Trp Phe Gln Gln Lys Pro Gly Thr Ser Pro
    50                  55                  60

Lys Phe Trp Ile Tyr Ser Thr Ser Ile Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95
```

-continued

```
Arg Met Glu Ala Glu Asp Ala Ala Thr Tyr Tyr Cys Gln Gln Arg Ser
            100                 105                 110

Ser Tyr Pro Pro Thr Phe Gly Ser Gly Thr Lys Leu Glu Ile Lys Gly
        115                 120                 125

Gly Gly Gly Ser Gly Gly Gly Gly Ser Gly Gly Gly Ser Gln Val
    130                 135                 140

Gln Leu Gln Gln Ser Gly Gly Glu Val Met Lys Pro Gly Ala Ser Val
145                 150                 155                 160

Lys Leu Ser Cys Lys Ala Thr Gly Tyr Thr Phe Thr Gly Tyr Trp Ile
                165                 170                 175

Glu Trp Ile Lys Gln Arg Pro Gly His Gly Leu Glu Trp Ile Gly Glu
            180                 185                 190

Ile Leu Pro Gly Ser Gly Gly Thr Asn Tyr Asn Glu Lys Phe Lys Gly
        195                 200                 205

Lys Ala Thr Phe Thr Ala His Thr Ser Ser Asn Thr Ala Tyr Met Gln
    210                 215                 220

Leu Ser Ser Leu Thr Thr Glu Asp Ser Ala Ile Tyr Tyr Cys Ala Arg
225                 230                 235                 240

Asp Ser Asn Ser Phe Thr Tyr Trp Gly Gln Gly Thr Leu Val Thr Val
                245                 250                 255

Ser Ser Thr Thr Thr Pro Ala Pro Arg Pro Pro Thr Pro Ala Pro Thr
        260                 265                 270

Ile Ala Ser Gln Pro Leu Ser Leu Arg Pro Glu Ala Cys Arg Pro Ala
    275                 280                 285

Ala Gly Gly Ala Val His Thr Arg Gly Leu Asp Phe Ala Cys Asp Ile
    290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
            355                 360                 365

Leu Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
        450                 455                 460

Ala Thr Lys Asp Thr Tyr Asp Ala Leu His Met Gln Ala Leu Pro Pro
465                 470                 475                 480

Arg
```

<210> SEQ ID NO 12
<211> LENGTH: 480
<212> TYPE: PRT
<213> ORGANISM: Homo sapiens -continued

<400> SEQUENCE: 12

```
Met Ala Leu Pro Val Thr Ala Leu Leu Leu Pro Leu Ala Leu Leu Leu
1               5                   10                  15

His Ala Ala Arg Pro Gln Ile Val Leu Thr Gln Ser Pro Ala Ile Met
                20                  25                  30

Ser Ala Ser Pro Gly Glu Lys Val Thr Ile Thr Cys Ser Val Ser Ser
            35                  40                  45

Ser Val Asp Tyr Ile His Trp Phe Gln Gln Lys Pro Gly Thr Ser Pro
        50                  55                  60

Lys Phe Trp Ile Tyr Ser Thr Ser Ile Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Met Glu Ala Glu Asp Ala Ala Thr Tyr Tyr Cys Gln Gln Arg Ser
            100                 105                 110

Ser Tyr Pro Pro Thr Phe Gly Ser Gly Thr Lys Leu Glu Ile Lys Gly
        115                 120                 125

Gly Gly Gly Ser Gly Gly Gly Gly Ser Gly Gly Gly Gly Ser Gln Val
    130                 135                 140

Gln Leu Gln Gln Ser Gly Gly Glu Val Met Lys Pro Gly Ala Ser Val
145                 150                 155                 160

Lys Leu Ser Cys Lys Ala Thr Gly Tyr Thr Phe Thr Gly Tyr Trp Ile
                165                 170                 175

Glu Trp Ile Lys Gln Arg Pro Gly His Gly Leu Glu Trp Ile Gly Glu
            180                 185                 190

Ile Leu Pro Gly Ser Gly Gly Thr Asn Tyr Asn Glu Lys Phe Lys Gly
        195                 200                 205

Lys Ala Thr Phe Thr Ala His Thr Ser Ser Asn Thr Ala Tyr Met Gln
    210                 215                 220

Leu Ser Ser Leu Thr Thr Glu Asp Ser Ala Ile Tyr Tyr Cys Ala Arg
225                 230                 235                 240

Asp Ser Asn Ser Phe Thr Tyr Trp Gly Gln Gly Thr Leu Val Thr Val
                245                 250                 255

Ser Ser Ala Ala Ala Ile Glu Val Met Tyr Pro Pro Pro Tyr Leu Asp
            260                 265                 270

Asn Glu Lys Ser Asn Gly Thr Ile Ile His Val Lys Gly Lys His Leu
        275                 280                 285

Cys Pro Ser Pro Leu Phe Pro Gly Pro Ser Lys Pro Phe Trp Val Leu
    290                 295                 300

Val Val Val Gly Gly Val Leu Ala Cys Tyr Ser Leu Leu Val Thr Val
305                 310                 315                 320

Ala Phe Ile Ile Phe Trp Val Arg Ser Lys Arg Ser Arg Leu Leu His
                325                 330                 335

Ser Asp Tyr Met Asn Met Thr Pro Arg Arg Pro Gly Pro Thr Arg Lys
            340                 345                 350

His Tyr Gln Pro Tyr Ala Pro Pro Arg Asp Phe Ala Ala Tyr Arg Ser
        355                 360                 365

Arg Val Lys Phe Ser Arg Ser Ala Asp Ala Pro Ala Tyr Gln Gln Gly
    370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
```

-continued

```
                    405                     410                     415

Pro Arg Arg Lys Asn Pro Gln Glu Gly Leu Tyr Asn Glu Leu Gln Lys
            420                     425                     430

Asp Lys Met Ala Glu Ala Tyr Ser Glu Ile Gly Met Lys Gly Glu Arg
        435                     440                     445

Arg Arg Gly Lys Gly His Asp Gly Leu Tyr Gln Gly Leu Ser Thr Ala
    450                     455                     460

Thr Lys Asp Thr Tyr Asp Ala Leu His Met Gln Ala Leu Pro Pro Arg
465                     470                     475                     480

<210> SEQ ID NO 13
<211> LENGTH: 237
<212> TYPE: PRT
<213> ORGANISM: Homo sapiens

<400> SEQUENCE: 13

Gln Val Gln Leu Gln Gln Ser Gly Gly Glu Val Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Gly Thr Asn Tyr Asn Glu Lys Phe
    50                  55                  60

Lys Gly Lys Ala Thr Phe Thr Ala His Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Asp Ser Asn Ser Phe Thr Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Gln Ile Val Leu Thr Gln Ser Pro Ala Ile Met Ser Ala
    130                 135                 140

Ser Pro Gly Glu Lys Val Thr Ile Thr Cys Ser Val Ser Ser Ser Val
145                 150                 155                 160

Asp Tyr Ile His Trp Phe Gln Gln Lys Pro Gly Thr Ser Pro Lys Phe
                165                 170                 175

Trp Ile Tyr Ser Thr Ser Ile Leu Ala Ser Gly Val Pro Ala Arg Phe
            180                 185                 190

Ser Gly Ser Gly Ser Gly Thr Ser Tyr Ser Leu Thr Ile Ser Arg Met
            195                 200                 205

Glu Ala Glu Asp Ala Ala Thr Tyr Tyr Cys Gln Gln Arg Ser Ser Tyr
    210                 215                 220

Pro Pro Thr Phe Gly Ser Gly Thr Lys Leu Glu Ile Lys
225                 230                 235

<210> SEQ ID NO 14
<211> LENGTH: 10
<212> TYPE: PRT
<213> ORGANISM: Homo sapiens

<400> SEQUENCE: 14

Gly Val Tyr Asp Gly Arg Glu His Thr Val
1               5                   10
```

```
<210> SEQ ID NO 15
<211> LENGTH: 481
<212> TYPE: PRT
<213> ORGANISM: Homo sapiens

<400> SEQUENCE: 15

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Gly Glu Val
                20                  25                  30

Met Lys Pro Gly Ala Ser Val Lys Leu Ser Cys Lys Ala Thr Gly Tyr
            35                  40                  45

Thr Phe Thr Gly Tyr Trp Ile Glu Trp Ile Lys Gln Arg Pro Gly His
        50                  55                  60

Gly Leu Glu Trp Ile Gly Glu Ile Leu Pro Gly Ser Gly Gly Thr Asn
65                  70                  75                  80

Tyr Asn Glu Lys Phe Lys Gly Lys Ala Thr Phe Thr Ala His Thr Ser
                85                  90                  95

Ser Asn Thr Ala Tyr Met Gln Leu Ser Ser Leu Thr Thr Glu Asp Ser
            100                 105                 110

Ala Ile Tyr Tyr Cys Ala Arg Asp Ser Asn Ser Phe Thr Tyr Trp Gly
            115                 120                 125

Gln Gly Thr Leu Val Thr Val Ser Ser Gly Gly Gly Ser Gly Gly
        130                 135                 140

Gly Gly Ser Gly Gly Gly Gly Ser Gln Ile Val Leu Thr Gln Ser Pro
145                 150                 155                 160

Ala Ile Met Ser Ala Ser Pro Gly Glu Lys Val Thr Ile Thr Cys Ser
                165                 170                 175

Val Ser Ser Ser Val Asp Tyr Ile His Trp Phe Gln Gln Lys Pro Gly
            180                 185                 190

Thr Ser Pro Lys Phe Trp Ile Tyr Ser Thr Ser Ile Leu Ala Ser Gly
            195                 200                 205

Val Pro Ala Arg Phe Ser Gly Ser Gly Ser Gly Thr Ser Tyr Ser Leu
        210                 215                 220

Thr Ile Ser Arg Met Glu Ala Glu Asp Ala Ala Thr Tyr Tyr Cys Gln
225                 230                 235                 240

Gln Arg Ser Ser Tyr Pro Pro Thr Phe Gly Ser Gly Thr Lys Leu Glu
                245                 250                 255

Ile Lys Ala Lys Pro Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
        290                 295                 300

Cys Asp Ile Tyr Ile Trp Ala Pro Leu Ala Gly Thr Cys Gly Val Leu
305                 310                 315                 320

Leu Leu Ser Leu Val Ile Thr Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
            355                 360                 365

Leu Arg Val Lys Phe Ser Arg Ser Ala Asp Ala Pro Ala Tyr Lys Gln
        370                 375                 380
```

```
Gly Gln Asn Gln Leu Tyr Asn Glu Leu Asn Leu Gly Arg Arg Glu Glu
385             390             395             400

Tyr Asp Val Leu Asp Lys Arg Arg Gly Arg Asp Pro Glu Met Gly Gly
            405             410             415

Lys Pro Arg Arg Lys Asn Pro Gln Glu Gly Leu Tyr Asn Glu Leu Gln
            420             425             430

Lys Asp Lys Met Ala Glu Ala Tyr Ser Glu Ile Gly Met Lys Gly Glu
        435             440             445

Arg Arg Arg Gly Lys Gly His Asp Gly Leu Tyr Gln Gly Leu Ser Thr
    450             455             460

Ala Thr Lys Asp Thr Tyr Asp Ala Leu His Met Gln Ala Leu Pro Pro
465             470             475             480

Arg

<210> SEQ ID NO 16
<211> LENGTH: 481
<212> TYPE: PRT
<213> ORGANISM: Homo sapiens

<400> SEQUENCE: 16

Met Ala Leu Pro Val Thr Ala Leu Leu Leu Pro Leu Ala Leu Leu Leu
1               5               10              15

His Ala Ala Arg Pro Gln Ile Val Leu Thr Gln Ser Pro Ala Ile Met
            20              25              30

Ser Ala Ser Pro Gly Glu Lys Val Thr Ile Thr Cys Ser Val Ser Ser
        35              40              45

Ser Val Asp Tyr Ile His Trp Phe Gln Gln Lys Pro Gly Thr Ser Pro
    50              55              60

Lys Phe Trp Ile Tyr Ser Thr Ser Ile Leu Ala Ser Gly Val Pro Ala
65              70              75              80

Arg Phe Ser Gly Ser Gly Ser Gly Thr Ser Tyr Ser Leu Thr Ile Ser
            85              90              95

Arg Met Glu Ala Glu Asp Ala Ala Thr Tyr Tyr Cys Gln Gln Arg Ser
            100             105             110

Ser Tyr Pro Pro Thr Phe Gly Ser Gly Thr Lys Leu Glu Ile Lys Gly
        115             120             125

Gly Gly Gly Ser Gly Gly Gly Gly Ser Gly Gly Gly Ser Gln Val
    130             135             140

Gln Leu Gln Gln Ser Gly Gly Glu Val Met Lys Pro Gly Ala Ser Val
145             150             155             160

Lys Leu Ser Cys Lys Ala Thr Gly Tyr Thr Phe Thr Gly Tyr Trp Ile
            165             170             175

Glu Trp Ile Lys Gln Arg Pro Gly His Gly Leu Glu Trp Ile Gly Glu
            180             185             190

Ile Leu Pro Gly Ser Gly Gly Thr Asn Tyr Asn Glu Lys Phe Lys Gly
        195             200             205

Lys Ala Thr Phe Thr Ala His Thr Ser Ser Asn Thr Ala Tyr Met Gln
    210             215             220

Leu Ser Ser Leu Thr Thr Glu Asp Ser Ala Ile Tyr Tyr Cys Ala Arg
225             230             235             240

Asp Ser Asn Ser Phe Thr Tyr Trp Gly Gln Gly Thr Leu Val Thr Val
            245             250             255

Ser Ser Ala Lys Pro Thr Thr Thr Pro Ala Pro Arg Pro Pro Thr Pro
        260             265             270
```

```
Ala Pro Thr Ile Ala Ser Gln Pro Leu Ser Leu Arg Pro Glu Ala Cys
    275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Lys Arg Gly Arg Lys Lys Leu Leu Tyr
                325                 330                 335

Ile Phe Lys Gln Pro Phe Met Arg Pro Val Gln Thr Thr Gln Glu Glu
                340                 345                 350

Asp Gly Cys Ser Cys Arg Phe Pro Glu Glu Glu Glu Gly Gly Cys Glu
                355                 360                 365

Leu Arg Val Lys Phe Ser Arg Ser Ala Asp Ala Pro Ala Tyr Lys Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
                435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg

<210> SEQ ID NO 17
<211> LENGTH: 482
<212> TYPE: PRT
<213> ORGANISM: Homo sapiens

<400> SEQUENCE: 17

Met Ala Leu Pro Val Thr Ala Leu Leu Leu Pro Leu Ala Leu Leu Leu
1               5                   10                  15

His Ala Ala Arg Pro Gln Ile Val Leu Thr Gln Ser Pro Ala Ile Met
                20                  25                  30

Ser Ala Ser Pro Gly Glu Lys Val Thr Ile Thr Cys Ser Val Ser Ser
            35                  40                  45

Ser Val Asp Tyr Ile His Trp Phe Gln Gln Lys Pro Gly Thr Ser Pro
    50                  55                  60

Lys Phe Trp Ile Tyr Ser Thr Ser Ile Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Met Glu Ala Glu Asp Ala Ala Thr Tyr Tyr Cys Gln Gln Arg Ser
                100                 105                 110

Ser Tyr Pro Pro Thr Phe Gly Ser Gly Thr Lys Leu Glu Ile Lys Gly
            115                 120                 125

Gly Gly Gly Ser Gly Gly Gly Gly Ser Gly Gly Gly Gly Ser Gln Val
    130                 135                 140

Gln Leu Gln Gln Ser Gly Gly Glu Val Met Lys Pro Gly Ala Ser Val
145                 150                 155                 160
```

-continued

```
Lys Leu Ser Cys Lys Ala Thr Gly Tyr Thr Phe Thr Gly Tyr Trp Ile
            165                 170                 175

Glu Trp Ile Lys Gln Arg Pro Gly His Gly Leu Glu Trp Ile Gly Glu
            180                 185                 190

Ile Leu Pro Gly Ser Gly Gly Thr Asn Tyr Asn Glu Lys Phe Lys Gly
            195                 200                 205

Lys Ala Thr Phe Thr Ala His Thr Ser Ser Asn Thr Ala Tyr Met Gln
            210                 215                 220

Leu Ser Ser Leu Thr Thr Glu Asp Ser Ala Ile Tyr Tyr Cys Ala Arg
225                 230                 235                 240

Asp Ser Asn Ser Phe Thr Tyr Trp Gly Gln Gly Thr Leu Val Thr Val
                245                 250                 255

Ser Ser Thr Thr Thr Pro Ala Pro Arg Pro Pro Thr Pro Ala Pro Thr
                260                 265                 270

Ile Ala Ser Gln Pro Leu Ser Leu Arg Pro Glu Ala Cys Arg Pro Ala
                275                 280                 285

Ala Gly Gly Ala Val His Thr Arg Gly Leu Asp Phe Ala Cys Asp Ile
            290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Cys Lys Arg Gly Arg Lys Lys Leu Leu
                325                 330                 335

Tyr Ile Phe Lys Gln Pro Phe Met Arg Pro Val Gln Thr Thr Gln Glu
                340                 345                 350

Glu Asp Gly Cys Ser Cys Arg Phe Pro Glu Glu Glu Glu Gly Gly Cys
                355                 360                 365

Glu Leu Arg Val Lys Phe Ser Arg Ser Ala Asp Ala Pro Ala Tyr Gln
            370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
        450                 455                 460

Thr Ala Thr Lys Asp Thr Tyr Asp Ala Leu His Met Gln Ala Leu Pro
465                 470                 475                 480

Pro Arg
```

```
<210> SEQ ID NO 18
<211> LENGTH: 15
<212> TYPE: PRT
<213> ORGANISM: Artificial Sequence
<220> FEATURE:
<223> OTHER INFORMATION: Gly Ser linker

<400> SEQUENCE: 18

Gly Gly Gly Gly Ser Gly Gly Gly Gly Ser Gly Gly Gly Gly Ser
1               5                   10                  15
```